US007749507B2

(12) United States Patent
Theisen et al.

(10) Patent No.: US 7,749,507 B2
(45) Date of Patent: Jul. 6, 2010

(54) MALARIA VACCINE

(75) Inventors: Michael Theisen, Frederiksberg (DK); Søren Jepsen, Holte (DK)

(73) Assignee: Statens Serum Institut, Copenhagen S (DK)

( * ) Notice: Subject to any disclaimer, the term of this patent is extended or adjusted under 35 U.S.C. 154(b) by 914 days.

(21) Appl. No.: 11/128,660

(22) Filed: May 12, 2005

(65) Prior Publication Data

US 2006/0024324 A1 Feb. 2, 2006

Related U.S. Application Data

(63) Continuation-in-part of application No. PCT/DK03/00759, filed on Nov. 6, 2003.

(30) Foreign Application Priority Data

Nov. 12, 2002 (DK) ................................ 2002 01741
Sep. 11, 2003 (DK) ................................ 2003 01307

(51) Int. Cl.
*A61K 39/00* (2006.01)
*A61K 39/38* (2006.01)
*A61K 39/295* (2006.01)
*A61K 38/00* (2006.01)

(52) U.S. Cl. .............. 424/192.1; 424/184.1; 424/191.1; 424/202.1; 530/300; 530/324

(58) Field of Classification Search ........................ None
See application file for complete search history.

(56) References Cited

U.S. PATENT DOCUMENTS 5,231,168 A * 7/1993 Dziegiel et al. ............. 530/350
2004/0096466 A1 * 5/2004 Druilhe et al. ............ 424/268.1

FOREIGN PATENT DOCUMENTS

WO WO 90/02811 3/1990
WO WO 00/50077 8/2000
WO WO 02/092628 A2 * 11/2002

OTHER PUBLICATIONS

Bowie et al (Science, 1990, 257:1306-1310).*
Greenspan et al. (Nature Biotechnology 7: 936-937, 1999).*
Carvalho et al., Scand. J. of Immunol., 56:327-343, 2002, abstract).*
Freshney (Culture of Animal Cells, A Manual of Basic Technique, Alan R. Liss, Inc., 1983, New York).*
Ballou et al., (Am. J. Trop. Med. Hyg. 71:239-247, 2004, p. 239).*
Soe-Soe et al., (Trans. Royal Soc. Trop. Med. Hyg. 95:81-84, 2001).*
Stenesh 1989, (The Dictionary of Biochemistry and Molecular Biology).*
Theisen et al (Vaccine 22:1188-1198, 2004, Online, Oct. 20, 2003).*
Carvalho et al., Scand. J. of Immunol., 56:327-343, 2002, abstract.*
Ballou et al., Am. J. Trop. Med. Hyg. 71:239-247, 2004, p. 239, Abstract.*
Soe-Soe et al., Trans. Royal Soc. Trop. Med. Hyg. 95:81-84, 2001, col. 1, paragraph1.*
Freshney (Culture of Animal Cells, A Manual of Basic Technique, Alan R. Liss, Inc., 1983, New York, p. 4).*
The Dictionary of Biochemistry and Molecular Biology, Stenesh, 1989.*
Carvalho et al (Mem Inst Cruz, Rio de Janelro, Vo. 94, Suppl. II, Nov. 1999)(Abstract only).*
Christian Boudin, et al., Possible Role Of Specific Immunoglobulin M Antibodies To *Plasmodium falciparum* Antigens In Immunoprotection Of Humans Living In A Hyperendemic Area, Burkina Faso, Journal of Clinical Microbiology, Mar. 1993, p. 636-641.
L. J. M. Carvalho, et al., Immunization Of *Saimirisciureus*, Monkeys With MSP-3 And GLURP, Two *Plasmodium falciparum* Antigens Targets Of Protective Antibodies, Mem Inst Oswaldo Cruz, Rio de Janeiro, vol. 94, Suppl. II, Nov. 1999.
L. J. M. Carvalho, et al., Malaria Vaccine: Candidate Antigens, Mechanisms, Constraints And Prospects, Scand. J. Immunol., 56, 2002, p. 327-343.
Daniel Dodoo, et al., Naturally Acquired Antibodies To The Glutamate-Rich Protein Are Associated With Protection Against *Plasmodium falciparum* Malaria, Journal Of Infectious Diseases, 2000, 181, p. 1202-1205.
Morten Dziegiel, et al., Immunoglobulin M And G Antibody Responses To *Plasmodium falciparum* Glutamate-Rich Protein: Correlation With Clinical Immunity In Gambian Children, Infection And Immunity, Jan. 1993, vol. 61, No. 1, p. 103-108.

(Continued)

*Primary Examiner*—Vanessa L. Ford
(74) *Attorney, Agent, or Firm*—Knobbe Martens Olson & Bear LLP

(57) ABSTRACT

A fusion protein, derived from *P. falciparum* Glutamate-rich protein (GLURP) genetically coupled to *P. falciparum* Merozoite surface protein 3 (MSP3) was produced in *Lactococcus lactis* as a secreted recombinant GLURP-MSP3 hybrid protein and experiments showed that the GLURP-part of the hybrid increased the overall antibody response. Immunizations with the hybrid protein consistently generated a stronger antibody response against the individual GLURP and MSP3 domains than a mixture of the two recombinant molecules injected at one site or the individual recombinant molecules injected simultaneously at two different sites. The difference was most pronounced for the MSP3-specific antibody response suggesting that T cell epitopes located in the GLURP R0-region provide help for B-cell epitopes in the MSP3 region. Moreover, when the animals were injected with a mixture of GLURP and MSP3, individual mice tended to mount a predominant antibody response against either molecule: in some animals GLURP was immunodominant whereas in other animals MSP3 was the dominant immunogen. Additionally, the hybrid was also more antigenic than the individual recombinant proteins since the ELISA-titer of naturally occurring IgG antibodies, in clinically immune African adults, against the hybrid protein was higher than the titers against the individual recombinant proteins. The hybrid protein was also demonstrated to be a potential protective antigen as mouse anti-GLURP-MSP3 IgG antibodies were able to inhibit parasite-growth in vitro in a monocyte-dependent manner.

5 Claims, 8 Drawing Sheets

OTHER PUBLICATIONS

Figure 1:
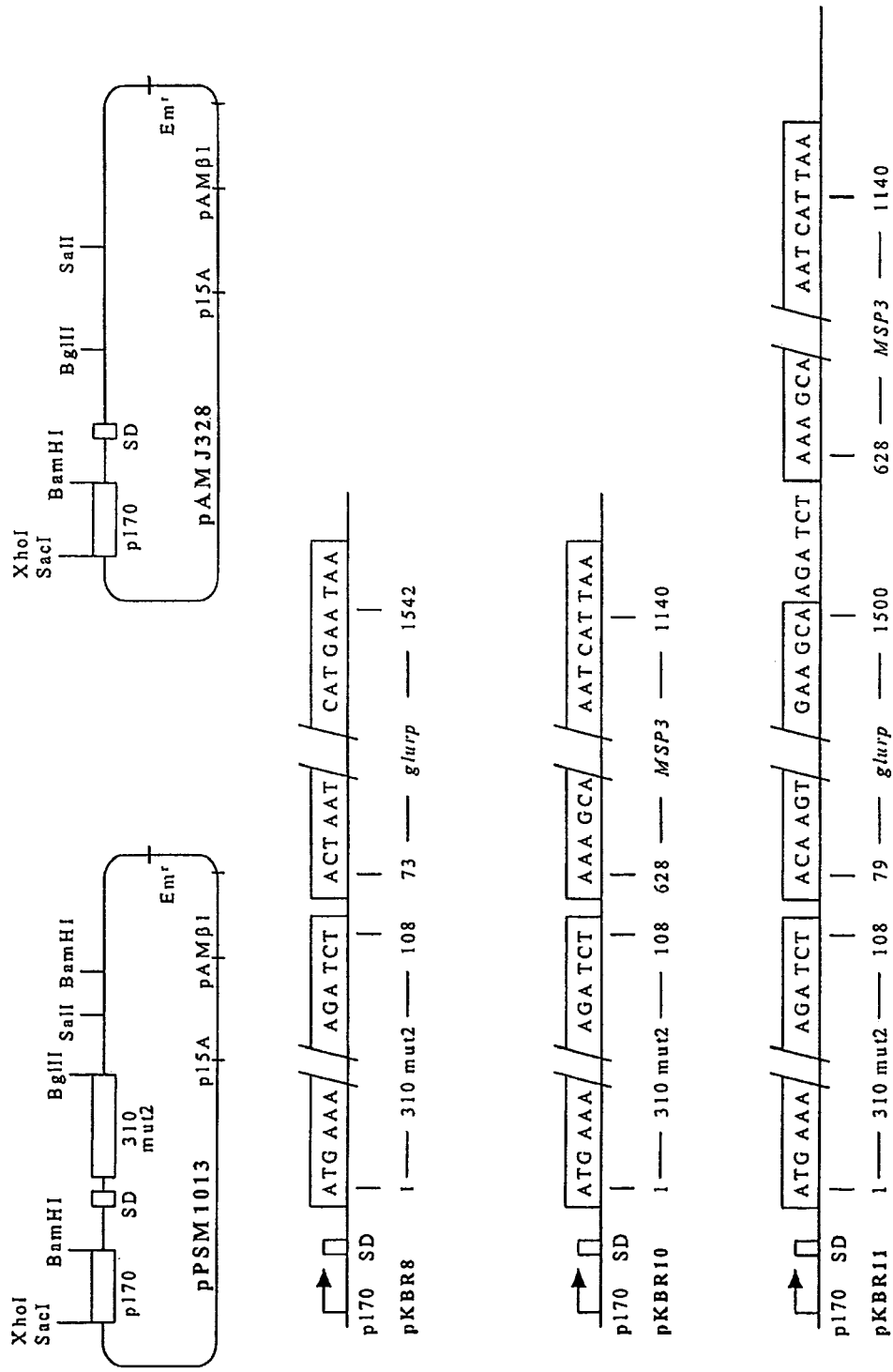

Claude Oeuvray, et al., Merozoite Surface Protein-3: A Malaria Protein Inducing Antibodies That Promote *Plasmodium falciparum* Killing By Cooperation With Blood Monocytes, Blood, vol. 84, No. 5, Sep. 1, 1994, p. 1594-1602.

Claude Oeuvray, et al., Cytophilic Immunoglobin Responses To *Plasmodium falciparum* Glutamate-Rich Protein Are Correlated With Protection Against Clinical Malaria In Dielmo, Senegal, Infection and Immunity, May 2000, vol. 86, No. 5, p. 2617-2620.

Karin de Sticker, et al., Conservation And Heterogeneity Of The Glutamate-Rich Protein (GLURP) Among Field Isolates And Laboratory Lines Of *Plasmodium falciparum*, Molecular And Biochemical Parasitology 111, 2000, p. 123-130.

Michael Theisen, et al., Identification Of A Major B-cell Epitope Of The *Plasmodium falciparum* Glutamate-Rich Protein (GLURP), Targeted By Human Antibodies Mediating Parasite Killing, Vaccine 19, 2001, p. 204-212.

Michael Theisen, et al., Immunogenicity Of The *Plasmodium falciparum* Glutamate-Rich Protein Expressed By Vaccinia Virus, Infection and Immunity, Aug. 1994, vol. 62, No. 8, p. 3270-3275.

Michael Theisen, et al., Selection Of Glutamate-Rich Protein Long Synthetic Peptides For Vaccine Development: Antigenicity and Relationship With Clinical Protection and Immunogenicity, Infection and Immunity, Sep. 2001, vol. 69, No. 9, p. 5223-5229.

Michael Theisen, et al., The Glutamate-Rich Protein (GLURP) Of *Plasmodium falciparum* Is A Target For Antibody-Dependent Monocyte-Mediated Inhibition Of Parasite Growth In Vitro, Infection And Immunity, Jan. 1998, vol. 66, No. 1, p. 11-17.

Michael Theisen, et al., Cloning, Nucleotide Sequencing And Analysis Of The Gene Encoding The Glutamate-Rich Protein (GLURP) From *Plasmodium reichenowi*, Molecular & Biochemical Parasitology 115, 2001, p. 269-273.

Michael Theisen, et al., Antigenicity and Immunogenicity of Recombinant Glutamate-Rich Protein of *Plasmodium falciparum* Expressed in *Escherichia coli*, Clinical and Diagnostic Laboratory Immunology, Jan. 1995, vol. 2, No. 1, p. 30-34.

L. J. M. Carvalho, et al., Immunization Of *Saimiri sciureus* Monkeys With A Recombinant Hybrid Protein Derived From The *Plasmodium falciparum* Antigen Glutamate-Rich Protein And Merozoite Surface Protein 3 Can Induce Partial Protection With Freund And Montanide ISA720 Adjuvants, Clinical And Diagnostic Laboratory Immunology (2005) vol. 12, No. 2, p. 242-248.

L. J. M. Carvalho, et al., Malaria Vaccine: Immunization Of *Saimiri sciureus* Monkeys With *Plasmodium falciparum* Merozoite Surface Protein-3 And Glutamate-Rich Protein Suggests That Protection Is Related To Antibody Levels, Scand. J. Immuno., 59, 2004, p. 363-372.

Cornelus C. Hermsen, et al., Glutamate-Rich Protein (GLURP) Induces Antibodies That Inhibit In Vitro Growth Of *Plasmodium falciparum* In A Phase 1 Malaria Trial, Vaccine (2006) p. 1-11.

Kiyotaka Kuzushima, et al., Efficient Identification Of HLA-A*2402-Restricted Cytomegalovirus-Specific CD8* T-Cell Epitopes By A Computer Algorithm And An Enzyme-Linked Immunospot Assay, Blood (2001) vol. 98, No. 6, p. 1872-1881.

Aribot, Georgette et al., "Pattern of Immunoglobulin Isotype Response to *Plasmodium falciparum* Blood-Stage Antigens in Individuals Living in a Holoendemic Area of Senegal (Dielmo, West Africa)" Am. J. Trop. Med. Hyg., 1996, pp. 449-457, vol. 54.

Aucan, Christophe et al., "High immunoglobulin G2 (lgG2) and Low lgG4 Levels are Associated with Human Resistance to *Plasmodium falciparum* Malaria" Infection and Immunity, Mar. 2000, pp. 1252-1258, vol. 68, No. 3.

Badell, Edgar et al., "Human Malaria in Immunocompromised Mice: An In Vivo Model to Study Defense Mechanisms against *Plasmodium falciparum*" J. Exp. Med., Dec. 4, 2000, pp. 1653-1659, vol. 192, No. 11.

Bouharoun-Tayoun, Hasnaa et al., "Antibodies that Protect Humans against *Plasmodium falciparum* Blood Stages Do not on their Own inhibit Parasite Growth and Invasion In Vitro, but Act in Cooperation with Monocytes" J. Exp. Med., Dec. 1990, pp. 1633-1641, vol. 172.

Bouharoun-Tayoun, Hasnaa et al., "Mechanisms Underlying the Monocyte-mediated Antibody-dependent Killing of *Plasmodium falciparum* Asexual Blood Stages" J. Exp. Med., Aug. 1995, pp. 409-418—vol. 182.

Boudin, Christian et al., "Possible Role of Specific Immunoglobulin M Antibodies to *Plasmodium falciparum* Antigens in Immunoprotection of Humans Living in a Hyperendemic Area, Burkina Faso" Journal of Clinical Microbiology, Mar. 1993, pp. 636-641, vol. 31, No. 3.

Bredmose, L. et al., "Development of a Heterologous Gene Expression System for Use in *Lactococcus Lactis*" A Novel Gram-positive Expression System, 2001, pp. 269-275.

Carvalho, L. J. M. et al., "Immunization of *Saimiri sciureus* Monkeys with *Plasmodium falciparum* Merozoite Surface Protein-3 and Glutamate-Rich Protein Suggests that Protection is Related to Antibody Levels" Scandinavian Journal of Immunolgoy, 2004, pp. 363-372, vol. 59.

Clark, John T. et al., "46-53 Kilodalton glycoprotein from the surface of *Plasmodium falciparum* merozoites" Molecular and Biochemical Parasitology, 1989, pp. 15-24, vol. 32.

Cohen, Dr. S. et al., "Gamma-Globulin and Acquired Immunity to Human Malaria" Nature, Nov. 25, 1961, pp. 733-737, vol. 192.

Dodoo, Daniel et al., "Naturally Acquired Antibodies to the Glutamate-Rich Protein Are Associated with Protection against *Plasmodium falciparum* Malaria" Journal of Infectious Diseases, Mar. 2000, pp. 1202-1205, vol. 181.

Druilhe, P. et al., "In vivo veritas: lessons from immunoglobulin-transfer experiments in malaria patients" Annals of Tripical Medicine and Parasitology, 1997, pp. S37-S53, vol. 91, Supplement No. 1.

Druilhe, Pierre et al., "Mechanisms of defense against *P. falciparum* asexual blood stages in humans" Immunology Letters, 1994, pp. 115-120, vol. 41.

Dziegiel, Morten et al., "Immunoglobulin M and G Antibody Responses to *Plasmodium falciparum* Glutamate-Rich Protein: Correlation with Clinical Immunity in Gambian Children" Infection and Immunity, Jan. 1993, pp. 103-108, vol. 61, No. 1.

Epping, Ronald J. et al., "An epitope recognized by inhibitory monoclonal antibodies that react with a 51 kilodalton merozoite surface antigen in *Plasmodium falciparum*" Molecular and Biochemical Parasitology, 1988, pp. 1-10, vol. 28.

Gasson, Michael J. "Plasmid Complements of *Streptococcus lactis* NCDO 712 and Other Lactic *Streptococci* After Protoplast-Induced Curing" Journal of Bacteriology, 1983, pp. 1-9, vol. 154, No. 1.

Genton, Blaise et al., "Safety and immunogenicity of a three-component blood-stage malaria vaccine in adults living in an endemic area of Papua New Guinea" Vaccine, 2000, pp. 2504-2511, vol. 18.

Gosselin, Edmund J. et al., "Enhanced Antigen Presentation Using Human Fcγ Receptor (Monocyte/Macrophage)-Specific Immunogens" The Journal of Immunology, Dec. 1, 1992, pp. 3477-3481, vol. 149, No. 11.

Hisaeda, Hajime et al., "Merozoite Surface Protein 3 and Protection against Malaria in *Aotus nancymai* Monkeys" The Journal of Infectious Diseases, 2002, pp. 657-664, vol. 185.

Hogh, Birthe et al., "Antibodies to a Recombinant Glutamate-Rich *Plasmodium falciparum* Protein: Evidence for Protection of Individuals Living in a Holoendemic Area of Liberia" Am. J. Trop. Med. Hyg., 1992, pp. 307-313, vol. 46.

Holo, Helge et al., "Transformation of *Lactococcus* by Electroporation" Methods in Molecular Biology, 1995, pp. 195-199, vol. 47.

Israelsen, Hans et al., "Cloning and Partial Characterization of Regulated Promoters from *Lactococcus lactis* Tn917-lacZ Integrants with the New Promoter Probe Vector, pAK80" Applied and Environmental Microbiology, Jul. 1995, pp. 2540-2547, vol. 61, No. 7.

Jensen, Peter Rugdal et al., "Minimal Requirements for Exponential Growth of *Lactococcus lactis*" Applied and Environmental Microbiology, Dec. 1993, pp. 4363-4366, vol. 59, No. 12.

Keitel, W.A. et al., "Phase I trial of two recombinant vaccines containing the 192kd carboxy terminal fragment of *Plasmodium falciparum* merozoite surface protein 1 (msp-$1_{19}$) and T helper epitopes of *Tetanus toxoid*" Vaccine, 2000, pp. 531-539, vol. 18.

Khusmith S. et al., "Antibody-dependent ingestion of *P. falciparum* merozoites by human blood monocytes" Parasite Immunology, 1983, pp. 357-368, vol. 5.

Klausen, J. et al., "Characterization of Purified Protein Derivative of Tuberculin by use of Monoclonal Antibodies: Isolation of a Delayed-Type Hypersensitivity Reactive Component from *M. tuberculosis* Culture Filtrate" Scand. J. Immunol., 1994, pp. 345-349, vol. 40.

Kussmann Martin et al., "Matrix-assisted Laser Desorption/Ionization Mass Spectrometric Peptide Mapping of the Neural Cell Adhesion Protein Neurolin Purified by Sodium Dodecyl Sulfate Polyacrylamide Gel Electrophoresis or Acidic Precipitation" Journal of Mass Spectrometry, 1997, pp. 483-493, vol. 32.

Lawrence, Gregor et al., "Effect of vaccination with 3 recombinant asexual-stage malaria antigens on initial growth rates of *Plasmodium falciparum* in non-immune volunteers" Vaccine, 2000, pp. 1925-1931, vol. 18.

Locher, Christopher et al., "Reduction of disulfide bonds in *Plasmodium falciparum* gp195 abolishes the production of growth-inhibitory antibodies" Vaccine, 1993, pp. 1119-1123, vol. 11, Issue 11.

Lunel, Francoise et al., "Effector Cells Involved in Nonspecific and Antibody-Dependant Mechanisms Directed against *Plasmodium falciparum* Blood Stages in Vitro" Infection and Immunity, Jul. 1989, pp. 2043-2049, vol. 57, No. 7.

Madsen, Søren Michael "Characterization of Regulated Promoters from *Lactococcus*" Ph. D. Thesis, Department of Lactic Acid Bacteria Biotechnological Institute, Hørsholm and Department of Microbiology The Technical University of Denmark, Jul. 2000.

Madsen, Søren M. et al., "Molecular characterization of the pH-inducible and growth phase-dependent promoter P170 of *Lactococcus lactis*" Molecular Microbiology, 1999, pp. 75-87, vol. 32.

McColl, Damian J. et al., "Molecular variation in a novel polymorphic antigen associated with *Plasmodium falciparum* merozoites" Molecular and Biochemical Parasitology, 1994, pp. 53-67, vol. 68.

McColl, Damian J et al., "Conservation of structural motifs and antigenic diversity in the *Plasmodium falciparum* merozoite surface protein-3 (MSP-3)" Molecular and Biochemical Parasitology, 1997, pp. 21-31, vol. 90.

Okenu, Daniel M.N., et al., "Allelic lineages of the merozoite surface protein 3 gene in *Plasmodium reichenowi* and *Plasmodium falciparum*" Molecular and Biochemical Parasitology, 2000, pp. 185-188, vol. 109.

Oeuvray, Claude et al., "Cytophilic Immunoglobulin Responses to *Plasmodium falciparum* Glutamate-Rich Protein Are Correlated with Protection against Clinical Malaria in Dielmo, Senegal" Infection and Immunity, May 2000, pp. 2617-2620, vol. 68, No. 5.

Oeuvray, Claude et al., "Natural immunity against *falciparum* malaria is strongly associated with lgG3 antibodies against the merozoite surface protein-3, in an age-independent manner" Cartagena, Colombia, XVth International Congress for Tropical Medicine and Malaria—Conference Proceeding, 2000.

Oeuvray, Claude et al., "Merozoite Surface Protein-3: A Malaria Protein Inducing Antibodies That Promote *Plasmodium falciparum* Killing by Cooperation With Blood Monocytes" Blood, Sep. 1, 1994, pp. 1594-1602, vol. 84, No. 5.

Rolph, Michael S. et al., "Recombinant viruses as vaccines and immunological tools" Current Opinion in Immunology, 1997, pp. 517-524, vol. 9.

Sabchareon, Arunee et al., "Parasitologic and Clinical Human Response to Immunoglobulin Administration in *falciparum* Malaria" Am. J. Trop. Med. Hyg., 1991, pp. 297-308, vol. 45.

Saul, Allan et al., "Human phase I vaccine trials of 3 recombinant asexual stage malaria antigens with Montanide ISA720 adjuvant" Vaccine, 1999, pp. 3145-3159, vol. 17.

Shevchenko, Andrej et al., "Mass Spectrometric Sequencing of Proteins from Silver-Stained Polyacrylamide Gels" Analytical Chemistry, Marcy 1, 1996, pp. 850-858, vol. 68, No. 5.

Shi, Ya Ping et al., "Fcγ Receptor IIa (CD32) Polymorphism Is Associated with Protection of Infants against High-Density *Plasmodium falciparum* Infection. VII. Asembo Bay Cohort Project" The Journal of Infectious Diseases, 2001, pp. 107-111, vol. 184.

Simon, Daniel et al., "Construction of a vector plasmid family and its use for molecular cloning in *Streptococcus lactis*" Biochimie, 1988, pp. 559-566, vol. 70.

Soe, Dr. Soe "Application of the antibody dependent cellular inhibition (ADCI) assay to the identification of protective antigens and the study of the establishment of protective immunity in Myanmar" Lille II University, Mar. 28, 2000, pp. 1-129, Lille, France.

Stricker, Karin De et al., "Conservation and heterogeneity of the glutamate-rich protein (GLURP) among field isolates and laboratory lines of *Plasmodium falciparum*" Molecular and Biochemical Parasitology, 2000, pp. 123-130, vol. 111.

Theisen, Michael et al., "Immunogenicity of the *Plasmodium falciparum* Glutamate-Rich Protein Expressed by Vaccinia Virus" Infection and Immunity, Aug. 1994, pp. 3270-3275, vol. 62, No. 8.

Theisen, Michael et al., "Antigenicity and Immunogenicity of Recombinant Glutamate-Rich Protein of *Plasmodium falciparum* Expressed in *Escherichia coli*" Clinical and Diagnostic Laboratory Immunology, Jan. 1995, pp. 30-34, vol. 2, No. 1.

Theisen, Michael et al., "The Glutamate-Rich Protein (GLURP) of *Plasmodium falciparum* Is a Target for Antibody-Dependent Monocyte-Mediated Inhibition of Parasite Growth In Vitro" Infection and Immunity, Jan. 1998, pp. 11-17, vol. 66, No. 1.

Theisen, Michael et al., "Identification of major B-cell epitope of the *Plasmodium falciparum* glutamate-rich protein (GLURP), targeted by human antibodies mediating parasite killing" Vaccine, 2001, pp. 204-212, vol. 19.

Theisen, Michael et al., "Selection of Glutamate-Rich Protein Long Synthetic Peptides for Vaccine Development: Antigenicity and Relationship with Clinical Protection and Immunogenicity" Infection and Immunity, Sep. 2001, pp. 5223-5229, vol. 69, No. 9.

Theisen, Michael et al., "Cloning, nucleotide sequencing and analysis of the gene encoding the glutamate-rich protein (GLURP) from *Plasmodium reichenowi*" Molecular & Biochemical Parasitology, 2001, pp. 269-273, vol. 115.

Thomas, Alan W. et al., "The Fab Fragments of Monoclonal lgG to a Merozoite Surface Antigen Inhibit *Plasmodium knowlesi* Invasion of Erythrocytes" Molecular and Biochemical Parasitology, 1984, pp. 187-199, vol. 13.

Warmerdam, Petra et al., "A Single Amino Acid in the Second lg-Like Domain of the Human Fcγ Receptor II is Critical for Human lgG2 Binding" The Journal of Immunology, Aug. 15, 1991, pp. 1338-1343, vol. 147.

World Health Organization "Weekly Epidemiological Record—Releve *Epidermiologique hebdomadaire*" Aug. 13, 1999, pp. 265-272, vol. 74.

* cited by examiner

A

B

GLURP-MSP3 Hybrid - Coverage 39%

AERSTSENRNKRIGGPKLRGNVTSNIKLPSNNKGKIIRGSNDELNKNSEDVLEQSEKSLVSENVPSGLDIDDIPKESIFIQEDQEGQTHSELNPETSEHSK
DLNNNDSKNESSDIISENNKSNKVQNHFESLSDLELLENSSQDNLDKDTISTEPFPNQKHKDLQQDLNDEPLEPFPTQIHKDYKEKNLINEEDSEPFPRQE
HKKVDNHNEEKNVFHENGSANGNQGSLKLKSFDEHLKDEKIENEPLVHENLSIPNDPIEQILNQPEQETNIQEQLYNEKQNVEEKQNSQIPSLDLKEPTNE
DILPNHNPLENIKQSESEINHVQDHALPKENIIDKLDNQKEHIDQSQHNINVLQENNINNHQLEPQEKPNIESFEPKNIDSEIILPENVETEEIIDDVPSP
KHSNHETFEEETSESEHEEAVSEKNAHETVEHEETVSQESNPEKADNDGNVSQNSNNELNENEFVESEKSEHEARSKAKEASSYDYILGWEFGGGVPEHKK
EENMLSHLYVSSKDKENISKENDDVLDEKEEEAEETEEEELEEKNEEETESEISEDEEEEEEEKEEENEKKKEQEKEQSNENNDQKKDMEAQNLISKNQN
NNEKNVKEAAESIMKTLAGLIKGNNQIDSTLKDLVEELSKYFKNH

GLURP - Coverage 30%

AERSTNTSENRNKRIGGPKLRGNVTSNIKFPSDNKGKIIRGSNDKLNKNSEDVLEQSEKSLVSENVPSGLDIDDIPKESIFIQEDQEGQTHSELNPETSEH
SKDLNNNGSKNESSDIISENNKSNKVQNHFESLSDLELLENSSQDNLDKDTISTEPFPNQKHKDLQQDLNDEPLEPFPTQIHKDYKEKNLINEEDSEPFPR
QKHKKVDNHNEEKNVFHENGSANGNQGSLKLKSFDEHLKDEKIENEPLVHENLSIPNDPIEQILNQPEQETNIQEQLYNEKQNVEEKQNSQIPSLDLKEPT
NEDILPNHNPLENIKQSESEINHVQDHALPKENIIDKLDNQKEHIDQSQHNINVLQENNINNHQLEPQEKPNIESFEPKNIDSEIILPENVETEEIIDDVP
SPKHSNHETFEEETSESEHEEAVSEKNAHETVEHEETVSQESNPEKADNDGNVSQNSNNELNENEFVESEKSEHEAAENEESSLEEGHHE

SEQUENCE LISTING

```
<160> NUMBER OF SEQ ID NOS: 11

<210> SEQ ID NO 1
<211> LENGTH: 651
<212> TYPE: PRT
<213> ORGANISM: Plasmodium falciparum

<400> SEQUENCE: 1

Ala Glu Arg Ser Thr Ser Glu Asn Arg Asn Lys Arg Ile Gly Gly Pro
1               5                   10                  15

Lys Leu Arg Gly Asn Val Thr Ser Asn Ile Lys Leu Pro Ser Asn Asn
            20                  25                  30

Lys Gly Lys Ile Ile Arg Gly Ser Asn Asp Glu Leu Asn Lys Asn Ser
        35                  40                  45

Glu Asp Val Leu Glu Gln Ser Glu Lys Ser Leu Val Ser Glu Asn Val
    50                  55                  60
```

-continued

```
Pro Ser Gly Leu Asp Ile Asp Ile Pro Lys Glu Ser Ile Phe Ile
 65                  70                  75                  80

Gln Glu Asp Gln Glu Gly Gln Thr His Ser Glu Leu Asn Pro Glu Thr
                 85                  90                  95

Ser Glu His Ser Lys Asp Leu Asn Asn Asn Asp Ser Lys Asn Glu Ser
            100                 105                 110

Ser Asp Ile Ile Ser Glu Asn Asn Lys Ser Asn Lys Val Gln Asn His
            115                 120                 125

Phe Glu Ser Leu Ser Asp Leu Glu Leu Leu Glu Asn Ser Ser Gln Asp
            130                 135                 140

Asn Leu Asp Lys Asp Thr Ile Ser Thr Glu Pro Phe Pro Asn Gln Lys
145                 150                 155                 160

His Lys Asp Leu Gln Gln Asp Leu Asn Asp Glu Pro Leu Glu Pro Phe
                165                 170                 175

Pro Thr Gln Ile His Lys Asp Tyr Lys Glu Lys Asn Leu Ile Asn Glu
                180                 185                 190

Glu Asp Ser Glu Pro Phe Pro Arg Gln Glu His Lys Lys Val Asp Asn
            195                 200                 205

His Asn Glu Glu Lys Asn Val Phe His Glu Asn Gly Ser Ala Asn Gly
            210                 215                 220

Asn Gln Gly Ser Leu Lys Leu Lys Ser Phe Asp Glu His Leu Lys Asp
225                 230                 235                 240

Glu Lys Ile Glu Asn Glu Pro Leu Val His Glu Asn Leu Ser Ile Pro
                245                 250                 255

Asn Asp Pro Ile Glu Gln Ile Leu Asn Gln Pro Glu Gln Glu Thr Asn
            260                 265                 270

Ile Gln Glu Gln Leu Tyr Asn Glu Lys Gln Asn Val Glu Glu Lys Gln
            275                 280                 285

Asn Ser Gln Ile Pro Ser Leu Asp Leu Lys Glu Pro Thr Asn Glu Asp
            290                 295                 300

Ile Leu Pro Asn His Asn Pro Leu Glu Asn Ile Lys Gln Ser Glu Ser
305                 310                 315                 320

Glu Ile Asn His Val Gln Asp His Ala Leu Pro Lys Glu Asn Ile Ile
                325                 330                 335

Asp Lys Leu Asp Asn Gln Lys Glu His Ile Asp Gln Ser Gln His Asn
            340                 345                 350

Ile Asn Val Leu Gln Glu Asn Asn Ile Asn Asn His Gln Leu Glu Pro
            355                 360                 365

Gln Glu Lys Pro Asn Ile Glu Ser Phe Glu Pro Lys Asn Ile Asp Ser
            370                 375                 380

Glu Ile Ile Leu Pro Glu Asn Val Glu Thr Glu Ile Ile Asp Asp
385                 390                 395                 400

Val Pro Ser Pro Lys His Ser Asn His Glu Thr Phe Glu Glu Thr
                405                 410                 415

Ser Glu Ser Glu His Glu Glu Ala Val Ser Glu Lys Asn Ala His Glu
            420                 425                 430

Thr Val Glu His Glu Glu Thr Val Ser Gln Glu Ser Asn Pro Glu Lys
            435                 440                 445

Ala Asp Asn Asp Gly Asn Val Ser Gln Asn Ser Asn Asn Glu Leu Asn
450                 455                 460

Glu Asn Glu Phe Val Glu Ser Glu Lys Ser Glu His Glu Ala Arg Ser
465                 470                 475                 480

Lys Ala Lys Glu Ala Ser Ser Tyr Asp Tyr Ile Leu Gly Trp Glu Phe
```

```
                    485                 490                 495
Gly Gly Gly Val Pro Glu His Lys Lys Glu Glu Asn Met Leu Ser His
                500                 505                 510

Leu Tyr Val Ser Ser Lys Asp Lys Glu Asn Ile Ser Lys Glu Asn Asp
            515                 520                 525

Asp Val Leu Asp Glu Lys Glu Glu Ala Glu Thr Glu Glu Glu
        530                 535                 540

Glu Leu Glu Glu Lys Asn Glu Glu Thr Glu Ser Glu Ile Ser Glu
545                 550                 555                 560

Asp Glu Glu Glu Glu Glu Glu Glu Lys Glu Glu Asn Glu Lys
                565                 570                 575

Lys Lys Glu Gln Glu Lys Glu Gln Ser Asn Glu Asn Asn Asp Gln Lys
            580                 585                 590

Lys Asp Met Glu Ala Gln Asn Leu Ile Ser Lys Asn Gln Asn Asn Asn
        595                 600                 605

Glu Lys Asn Val Lys Glu Ala Ala Glu Ser Ile Met Lys Thr Leu Ala
    610                 615                 620

Gly Leu Ile Lys Gly Asn Asn Gln Ile Asp Ser Thr Leu Lys Asp Leu
625                 630                 635                 640

Val Glu Glu Leu Ser Lys Tyr Phe Lys Asn His
            645                 650

<210> SEQ ID NO 2
<211> LENGTH: 1953
<212> TYPE: DNA
<213> ORGANISM: Plasmodium falciparum

<400> SEQUENCE: 2
gccgaaagat ctacaagtga gaatagaaat aaacgaatcg ggggtcctaa attaaggggt       60
aatgttacaa gtaatataaa gctgccatca ataacaaag gtaaaattat aagaggttcg       120
aatgatgaac ttaataaaaa ctctgaagat gttttagaac aaagcgaaaa atcgcttgtt      180
tcagaaaatg ttcctagtgg attagatata atgatatcc ctaaagaatc tatttttatt      240
caagaagatc aagaaggtca aactcattct gaattaaatc ctgaaacatc agaacatagt      300
aaagatttaa ataataatga ttcaaaaaat gaatctagtg atattattc agaaaataat      360 aaatcaaata agtacaaaa tcattttgaa tcattatcag atttagaatt acttgaaaat      420
tcctcacaag ataatttaga caagataca atttcaacag aaccttttcc taatcaaaaa      480
cataaagact acaacaaga tttaaatgat gaaccttag aacccttcc tacacaaata       540 cataaagatt ataagaaaa aaatttaata aatgaagaag attcagaacc atttcccaga      600
caagagcata aaaaggtaga caatcataat gaagaaaaaa acgtatttca tgaaaatggt      660
tctgcaaatg gtaatcaagg aagtttgaaa cttaaatcat tcgatgaaca tttaaaagat      720
gaaaaaatag aaaatgaacc acttgttcat gaaaatttat ccataccaaa tgatccaata      780
gaacaaatat taaatcaacc tgaacaagaa acaaatatcc aggaacaatt gtataatgaa      840
aaacaaaatg ttgaagaaaa acaaaattct caaatacctt cgttagattt aaaagaacca      900
acaaatgaag atattttacc aaatcataat ccattagaaa atataaaaca agtgaatca       960 gaaataaatc atgtacaaga tcatgcgcta ccaaaagaga atataataga caaacttgat     1020
aatcaaaaag aacacatcga tcaatcacaa cataatataa atgtattaca agaaaataac     1080
ataaacaatc accaattaga acctcaagag aaacctaata ttgaatcgtt tgaacctaaa     1140
aatatagatt cagaaattat tcttcctgaa aatgttgaaa cagaagaaat aatagatgat     1200
```

-continued

```
gtgccttccc ctaaacattc taaccatgaa acatttgaag aagaaacaag tgaatctgaa    1260
catgaagaag ccgtatctga aaaaaatgcc cacgaaactg tcgaacatga agaaactgtg    1320
tctcaagaaa gcaatcctga aaaagctgat aatgatggaa atgtatctca aaacagcaac    1380
aacgaattaa atgaaaatga attcgttgaa tcggaaaaaa gcgagcatga agcaagatct    1440
aaagcaaaag aagcttctag ttatgattat attttaggtt gggaatttgg aggaggcgtt    1500
ccagaacaca aaaagaaga aaatatgtta tcacatttat atgtttcctc aaaggataag     1560
gaaaatatat ctaaggaaaa tgatgatgta ttagatgaga aggaagaaga ggcagaagaa    1620
acagaagaag aagaacttga agaaaaaaat gaagaagaaa cagaatcaga ataagtgaa     1680 gatgaagaag aagaagaaga agaagaaaag gaagaagaaa atgaaaaaaa aaagaacaa     1740 gaaaagaac aaagtaatga gaataatgat caaaaaaag atatggaagc acagaattta      1800
atttctaaaa accagaataa taatgagaaa aacgtaaaag aagctgctga agcatcatg     1860 aaaactttag ctggtttaat caagggaaat aatcaaatag attctacctt aaaagattta    1920
gtagaagaat tatccaaata ttttaaaaat cat                                  1953
```

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
cccagatcta caagtgagaa tagaaataaa c                                    31

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
cccagatctt gcttcatgct cgcttttttc cgat                                 34

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
aagtagatct actaatacaa gtgagaatag aaataaac                             38

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
gttcagatct ttattcatga tggccttcta gc                                   32

```
<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
cccagatcta aagcaaaaga agcttctagt tat                                    33

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
attagatctc atttaatgat ttttaaaata tttggata                               38

<210> SEQ ID NO 9
<211> LENGTH: 96
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9
```

Arg Lys Thr Lys Glu Tyr Ala Glu Lys Ala Lys Asn Ala Tyr Glu Lys
 1               5                  10                  15

Ala Lys Asn Ala Tyr Gln Lys Ala Asn Gln Ala Val Leu Lys Ala Lys
            20                  25                  30

Glu Ala Ser Ser Tyr Asp Tyr Ile Leu Gly Trp Glu Phe Gly Gly Gly
        35                  40                  45

Val Pro Glu His Lys Lys Glu Glu Asn Met Leu Ser His Leu Tyr Val
    50                  55                  60

Ser Ser Lys Asp Lys Glu Asn Ile Ser Lys Glu Asn Asp Asp Val Leu
65                  70                  75                  80

Asp Glu Lys Glu Glu Glu Ala Glu Glu Thr Glu Glu Glu Leu Glu
                85                  90                  95

```
<210> SEQ ID NO 10
<211> LENGTH: 129
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10
```

Asn Val Pro Ser Gly Leu Asp Ile Asp Ile Pro Lys Glu Ser Ile
 1               5                  10                  15

Phe Ile Gln Glu Asp Gln Glu Gly Gln Thr His Ser Glu Leu Asn Pro
            20                  25                  30

Glu Thr Ser Glu His Ser Lys Asp Leu Asn Asn Asn Gly Ser Lys Asn
        35                  40                  45

Glu Ser Ser Asp Ile Ile Ser Glu Asn Asn Lys Ser Asn Lys Val Gln
    50                  55                  60

Asn His Phe Glu Ser Leu Ser Asp Leu Glu Leu Leu Glu Asn Ser Ser

-continued

```
                65                  70                  75                  80
Gln Asp Asn Leu Asp Lys Asp Thr Ile Ser Thr Glu Pro Phe Pro Asn
                    85                  90                  95
Gln Lys His Lys Asp Leu Gln Gln Asp Leu Asn Asp Glu Pro Leu Glu
                100                 105                 110
Pro Phe Pro Thr Gln Ile His Lys Asp Tyr Lys Glu Lys Asn Leu Ile
        115                 120                 125
Asn

<210> SEQ ID NO 11
<211> LENGTH: 494
<212> TYPE: PRT
<213> ORGANISM: Plasmodium falciparum

<400> SEQUENCE: 11

Ala Glu Arg Ser Thr Asn Thr Ser Glu Asn Arg Asn Lys Arg Ile Gly
1               5                   10                  15
Gly Pro Lys Leu Arg Gly Asn Val Thr Ser Asn Ile Lys Phe Pro Ser
                20                  25                  30
Asp Asn Lys Gly Lys Ile Ile Arg Gly Ser Asn Asp Lys Leu Asn Lys
            35                  40                  45
Asn Ser Glu Asp Val Leu Glu Gln Ser Glu Lys Ser Leu Val Ser Glu
        50                  55                  60
Asn Val Pro Ser Gly Leu Asp Ile Asp Ile Pro Lys Glu Ser Ile
65                  70                  75                  80
Phe Ile Gln Glu Asp Gln Glu Gly Gln Thr His Ser Glu Leu Asn Pro
                85                  90                  95
Glu Thr Ser Glu His Ser Lys Asp Leu Asn Asn Gly Ser Lys Asn
                100                 105                 110
Glu Ser Ser Asp Ile Ile Ser Glu Asn Asn Lys Ser Asn Lys Val Gln
        115                 120                 125
Asn His Phe Glu Ser Leu Ser Asp Leu Glu Leu Leu Glu Asn Ser Ser
    130                 135                 140
Gln Asp Asn Leu Asp Lys Asp Thr Ile Ser Thr Glu Pro Phe Pro Asn
145                 150                 155                 160
Gln Lys His Lys Asp Leu Gln Gln Asp Leu Asn Asp Glu Pro Leu Glu
                165                 170                 175
Pro Phe Pro Thr Gln Ile His Lys Asp Tyr Lys Glu Lys Asn Leu Ile
            180                 185                 190
Asn Glu Glu Asp Ser Glu Pro Phe Pro Arg Gln Lys His Lys Lys Val
        195                 200                 205
Asp Asn His Asn Glu Lys Asn Val Phe His Glu Asn Gly Ser Ala
    210                 215                 220
Asn Gly Asn Gln Gly Ser Leu Lys Leu Lys Ser Phe Asp Glu His Leu
225                 230                 235                 240
Lys Asp Glu Lys Ile Glu Asn Glu Pro Leu Val His Glu Asn Leu Ser
                245                 250                 255
Ile Pro Asn Asp Pro Ile Glu Gln Ile Leu Asn Gln Pro Glu Gln Glu
            260                 265                 270
Thr Asn Ile Gln Glu Gln Leu Tyr Asn Glu Lys Gln Asn Val Glu Glu
        275                 280                 285
Lys Gln Asn Ser Gln Ile Pro Ser Leu Asp Leu Lys Glu Pro Thr Asn
    290                 295                 300
Glu Asp Ile Leu Pro Asn His Asn Pro Leu Glu Asn Ile Lys Gln Ser
```

-continued

```
305                 310                 315                 320
Glu Ser Glu Ile Asn His Val Gln Asp His Ala Leu Pro Lys Glu Asn
                325                 330                 335
Ile Ile Asp Lys Leu Asp Asn Gln Lys Glu His Ile Asp Gln Ser Gln
            340                 345                 350
His Asn Ile Asn Val Leu Gln Glu Asn Asn Ile Asn Asn His Gln Leu
            355                 360                 365
Glu Pro Gln Glu Lys Pro Asn Ile Glu Ser Phe Glu Pro Lys Asn Ile
        370                 375                 380
Asp Ser Glu Ile Ile Leu Pro Glu Asn Val Glu Thr Glu Glu Ile Ile
385                 390                 395                 400
Asp Asp Val Pro Ser Pro Lys His Ser Asn His Glu Thr Phe Glu Glu
                405                 410                 415
Glu Thr Ser Glu Ser Glu His Glu Glu Ala Val Ser Glu Lys Asn Ala
            420                 425                 430
His Glu Thr Val Glu His Glu Glu Thr Val Ser Gln Glu Ser Asn Pro
            435                 440                 445
Glu Lys Ala Asp Asn Asp Gly Asn Val Ser Gln Asn Ser Asn Asn Glu
    450                 455                 460
Leu Asn Glu Asn Glu Phe Val Glu Ser Glu Lys Ser Glu His Glu Ala
465                 470                 475                 480
Ala Glu Asn Glu Glu Ser Ser Leu Glu Glu Gly His His Glu
                485                 490
```

MALARIA VACCINE

INCORPORATION BY REFERENCE

This application is a continuation-in-part of International Patent Application PCT/DK2003/000759 filed Nov. 6, 2003 and published as WO 2004/043488 on May 27, 2004, which claims priority from Denmark Application Numbers PA 2002 01741 filed Nov. 12, 2002 and PA 2003 01307 filed Sep. 11, 2003.

Each of the above-referenced applications, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. Patent law; e.g., they can mean "includes", "included", "including" and the like. Terms such as "consisting essentially of" and "consists essentially of" have the meaning attributed to them in U.S. Patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. Patent law; namely, that these terms are closed ended.

FIELD OF INVENTION

An antigen based vaccine against malaria comprising fusion proteins derived from *Plasmodium falciparum* Glutamate-rich protein (GLURP) genetically coupled to at least one other *Plasmodium falciparum* derived protein, e.g. the Merozoite surface protein 3 (MSP3), or a vaccine comprising the DNA encoding this fusion protein and the production of such a vaccine.

BACKGROUND

Malaria is affecting 40% of the world's population with an estimated 1.5-2.7 million deaths annually (57). This represents a tremendous human suffering and a burden that prevents the development of the affected endemic communities. Malaria is now almost confined to the poorest tropical areas of Africa, Asia and Latin America, but transmission is being reintroduced to areas where it had previously been eradicated. Malaria is one of the world's greatest public health problems.

The increasing emerging of insecticide resistant vectors and drug resistant parasites calls for investment in new and better control tools. Malaria vaccines hold the potential to dramatically alleviate the burden of malaria. However, our understanding of the mechanisms underlying protective immunity is incomplete hence specific markers of protection still needs to be defined.

An effective malaria vaccine will require the induction of appropriate humoral and cellular immune responses, against several key parasite antigens expressed during the various stages of the parasite life cycle. Each stage in the life cycle provides an opportunity for a vaccine.

Two lines of evidence suggest that a malaria vaccine is attainable:

Firstly, it is a well-established observation that repeated exposure to malaria parasites can lead to the development of solid clinical immunity, a status of premunition with concomitant existence of parasites and protective antibodies. Clinically immune individuals generally have a lower parasite density and the immunity is quite effective at reducing mortality.

Secondly, experiments in humans as well as in animal models have established that immunizations can induce immunity against subsequent challenge with parasites suggesting that vaccination can become a realistic tool for malaria control.

In now classical experiments, Cohen and colleagues demonstrated that the passive transfer of antibodies purified from clinically immune individuals could ameliorate acute malaria attacks in African children with life-threatening *P. falciparum* infections (10). Druilhe and coworkers confirmed Cohen's results (42). They showed that IgG from clinically malaria immune West Africans were able—in a strain-independent manner—to substantially decrease the parasite load in asymptomatic Thai children with drug resistant *P. falciparum* malaria.

These groundbreaking passive transfer experiments have proven that antibodies are crucial in reducing/eliminating the asexual stage parasite load.

However, in vitro investigations with the same "protective" IgG preparations (42) demonstrated that antibodies do not inhibit parasite growth on their own, but act synergistically with blood mononuclear cells to control parasite multiplication (5). This parasite containing mechanism is referred to as antibody-dependent cellular inhibition (ADCI) (5, 26, 31). Recent studies have further demonstrated that binding of cytophilic antibodies such as IgG1 and IgG3 in conjunction with blood mononuclear cells via their FcγIIa receptors trigger the release of killing factors such as tumor necrosis factor-α (6).

Immuno-epidemiological studies support the in vivo relevance of a monocyte-dependent, antibody-mediated mechanism by showing a correlation between the acquisition of clinical immunity and levels of IgG1 and IgG3 antibodies, which bind well to the monocyte FcγRIIa receptor (1, 41). The putative involvement of this receptor in the development of immunity against clinical malaria is also supported by the finding that allelic polymorphism in FcγRIIa is associated with differential susceptibility to *P. falciparum* malaria (45). Kenyan infants homozygous for the FcγRIIa-Arg131 allele are reported to be less at risk from high-density *P. falciparum* infections compared with children with the heterozygous Arg/His131 genotype (45). Since the FcγIIa-Arg131 genotype (but not the FcγIIa-His131 genotype) binds strongly to IgG1 and IgG3, this finding supports the notion that monocyte-mediated killing of *P. falciparum* is an important mechanism for parasite containment in vivo. Additionally, Aucan et al (2) found that levels of specific IgG2 antibodies—but not IgG3 and IgG1—were associated with protection from clinical malaria in a population from Bukina Faso. Subsequent sequencing of FcγRIIa revealed that 70% of the study subjects had the FcγRIIa-H131 allele. This allele binds strongly to IgG2 (56), suggesting that IgG2 is acting as a cytophilic subclass in this population (2). Collectively these observations suggest that the FcγRIIa genotype is an important factor for the development of immunity to clinical malaria and lends support to the validity of in vitro ADCI model.

The development of a vaccine for malaria has become increasingly recognized as a high priority in the effort to control malaria worldwide due to the increasing incidence of drug-resistant disease. New tools are therefore required to facilitate the clinical evaluation of candidate vaccines, particular the validation of in vitro correlates of the protection afforded by vaccination. ADCI may provide one such tool (13). The currently most prominent blood-stage vaccine candidates MSP1, MSP2, AMA1, and RESA have primarily been selected for clinical testing because of their ability to induce growth-inhibitory antibodies in pre-clinical animal models (9, 16, 16, 30, 55). However, despite initial promises, they have in general proved poorly immunogenic in the human volunteers (18, 25, 29, 43) and the induced antibodies were unable to inhibit the in vitro growth of *P. falciparum*. Thus, the in vitro invasion inhibition assay is not ready to serve as a surrogate marker of immunity.

The lack of suitable correlates of human protection that reflect inhibition of merozoite invasion has encouraged the development of other in vitro models that reflect possible killing mechanisms in clinically immune individuals. Druilhe and coworkers have hypothesized that antibodies act synergistically with human blood monocytes to control parasite growth in vivo and have accordingly developed the in vitro correlate of this killing mechanism—the ADCI assay. We have so far identified two antigens—GLURP and MSP3—that are targets of ADCI-effective human antibodies.

The *Plasmodium falciparum* Glutamate-rich protein (GLURP) and the Merozoite surface protein 3 (MSP3) are both targeted by human IgG antibodies, which can inhibit parasite growth in vitro in a monocyte-dependent manner (36, 52) and in vivo in the humanized SCID mouse model (3). The similar effects of human antibodies against these antigens are also suggested by a number of immuno-epidemiological studies, which demonstrate that the levels of GLURP and MSP3 specific cytophilic antibodies (IgG1 and IgG3) are significantly associated with a reduced risk of malaria attacks (11, 38, 50).

The discovery of GLURP and MSP3 is based on the in vitro analysis of passive transfer of immunity by purified African Immunoglobulin G (5, 6, 14, 42). These investigations have led to the elucidation of a putative effector mechanism in the defense against *P. falciparum* malaria (12), and the subsequent identification of the involved parasite molecules. The major B-cell epitopes recognized by these human IgG antibodies have been localized to conserved sequences in the $GLURP_{27-489}$ and $MSP3_{212-257}$ regions, respectively (36, 50, 51). These studies lead to the identification of the N-terminal region of GLURP ($GLURP_{27-489}$) (52) and the C-terminal region of MSP3, ($MSP3_{210-380}$) (36) as targets of biologically active antibodies.

Different regions of these antigens have previously been produced in *Escherichia coli* fused to various affinity-tags (35, 53, 54). Whereas such additional sequences are advantageous for purification they also pose a potential problem because host immune responses against such sequences may render them useless for repeated applications.

Immune epidemiological investigations confirmed the relevance of anti-GLURP and anti-MSP3 IgG antibodies to acquired protection:

For GLURP, three independent studies performed in Dielmo, Senegal (38), Dodowa, Ghana (11, 50) and OoDo, Myanmar (Soe Soe, unpublished) have demonstrated a statistically significant correlation between levels of GLURP-specific IgG3 and/or IgG1 antibodies and protection against malaria attack. This association was highly significant even after controlling for the confounding effect of age-related exposure to *P. falciparum*. These results confirm previous studies, which found that naturally occurring IgG antibodies to GLURP are associated with protection against disease in Gambian children (15) and against high levels of parasitemia in children from Liberia (21) and Burkina Faso (4).

For MSP3, a high ratio (>2) of cytophilic to non-cytophilic antibodies (IgG1+IgG3/IgG2+IgG4+IgM) allowed to distinguish individuals without recorded malaria attacks from individuals with malaria attacks. This was found in every age group among approximately 200 villagers from Dielmo who have been under daily clinical surveillance for more then 8 years (37). At the individual level, the occurrence of anti-MSP3 IgG3 antibodies was strongly associated with protection, in contrast to antibodies of other isotypes directed against the same molecule or antibodies of any isotype directed against 5 other antigens (37).

A similar consistency in seroepidemiological data is not common for any other malaria vaccine candidate as exemplified by MSP1, the hitherto leading candidate as a vaccine against *P. falciparum* malaria.

The major B-ell epitopes recognized by these human IgG antibodies have been localized to conserved sequences in the $GLURP_{27-489}$ and $MSP3_{212-257}$ regions, respectively (36, 50, 51). These studies lead to the identification of the N-terminal region of GLURP ($GLURP_{27-489}$) (52) and the C-terminal region of MSP3, ($MSP3_{210-380}$) (36) as targets of biologically active antibodies.

Sequence analyses of the $GLURP_{27-489}$ and $MSP3_{210-380}$ regions from 44 field isolates and laboratory lines of *P. falciparum* show that defined epitopes in GLURP (P1, P3, and P4) (48) and MSP3 (b peptide) (34), which are targeted by ADCI-effective human antibodies are almost completely conserved, suggesting that they are functionally constrained and not subject to selection for variation at the amino acid level. Of the different epitopes in the $GLURP_{27-489}$ region, P3 might be the most important, since affinity-purified human antibodies against the P3 peptide mediated the strongest ADCI-effect in vitro (51). The conservation of major B-cell epitopes in GLURP and MSP3 is further supported by the observation that they are almost identical between *P. falciparum* and the closely related parasite *Plasmodium reichenowi*; a natural parasite for Chimpanzees (39, 53), and that plasma IgG antibodies from 71 adult Liberians clinically immune to malaria display identical binding patterns towards recombinant proteins representing the $GLURP_{27-500}$ regions from both species (53).

Collectively, these findings demonstrate that GLURP and MSP3 B-cell epitopes recognized by biologically effective human antibodies are conserved between geographically distant *P. falciparum* isolates and functionally constrained, suggesting that a vaccine based on GLURP and MSP3 may protect against a broad range of parasite strains worldwide.

In vitro experiments showed that naturally occurring affinity-purified human antibodies to GLURP (52) and MSP3 (36) could inhibit parasite growth in a monocyte-dependent manner, whereas control antibodies affinity-purified on 7 other malarial vaccine candidates were unable to exert a similar effect (47).

The same inhibitory effect was obtained using naturally occurring affinity-purified IgG antibodies against both recombinant proteins ($GLURP_{27-489}$, and $GLURP_{705-1178}$) (52) and synthetic peptides derived from the GLURP R0 region, P3 ($GLURP_{93-207}$), S3 ($GLURP_{407-434}$), and LR67 ($GLURP_{85-312}$) (50, 51), respectively.

In vivo experiments where affinity-purified MSP3b-specific human antibodies were passively transferred into *P. falciparum* infected Hu-RBC BXN mice, showed a parasite clearance as fast as that induced by Chloroquine, and faster than that induced by total African IgG (3). The latter observation indicates that immunization with selected antigens may lead to stronger immunity than that induced by the whole parasite (3).

In vivo experiments where *Aotus* monkeys immunized with recombinant MSP3 in Freunds complete adjuvant were fully protected against an experimental *P. falciparum* challenge (20). Immunizations of *Saimiri sciureus* monkeys have demonstrated that $GLURP_{27-500}$ adsorbed to $Al(OH)_3$ is nontoxic, immunogenic and elicit high titers of anti-GLURP antibodies which recognize *P. falciparum* by IFA (8). In a subsequent challenge with *P. falciparum* infected erythrocytes, two out of three monkeys were partially protected, this effect being directly related to the titer and epitope specificity of the antibodies developed by the primates in response to the immunogen (8).

These findings strongly support the notion that immune responses against GLURP and MSP3 B-cell epitopes that elicit ADCI-effective antibodies controls parasite multiplication in vivo.

Different regions of these antigens have previously been produced in *Escherichia coli* fused to various affinity-tags (35, 53, 54). Whereas such additional sequences are advantageous for purification they also pose a potential problem because host immune responses against such sequences may render them useless for repeated applications. It is therefore desirable to explore expression systems, which aims to produce the recombinant protein without a vector-encoded affinity-tag.

A restricted number of formulations based on MSP3 and GLURP have been select for further vaccine development and studied at the pre-clinical level first in mice (49, 54) and then in non-human primates challenged with *P. falciparum* (8). The N-terminal region of GLURP and the C-terminal region of MSP3 proved strongly immunogenic in pre-clinical models. These have now been produced individually using a new, highly efficient, expression system based on the pH and growth phase regulated promoter, P170, from *Lactococcus lactis* (23, 33).

We have so far identified two antigens—GLURP and MSP3—that are targets of ADCI-effective human antibodies and recently performed two clinical phase I trials with the individual antigens. Both vaccines induced strong cellular responses in the volunteers, whereas the IgG antibody responses were moderate. All volunteers from the GLURP trial generated antibodies against the P3 B-cell epitopes, which is the most prominent target of ADCI-effective antibodies in clinically immune individuals. The relatively low levels of vaccine-induced antibodies may be related to the limited number of B-cell epitopes on the GLURP synthetic peptides.

It is therefore, desirable to develop a vaccine based on a recombinant protein, which include GLURP and MSP3 preferably with neighboring sequences containing additional B- and T-cell epitopes or other antigens from *P. falciparum* such as the CS-antigen. It is also desirable to use expression systems, which produces the recombinant protein without a vector-encoded affinity-tag, such as *L. lactis*.

SUMMARY OF THE INVENTION

A vaccine against malaria, which has an improved vaccine-induced antibody expression, is disclosed. The vaccine comprises a fusion protein derived from *Plasmodium falciparum* Glutamate-rich protein (GLURP) genetically coupled to at least one other *Plasmodium falciparum* derived protein, e.g. the Merozoite surface protein 3 (MSP3), or the corresponding nucleotide sequence coding said fusion protein.

DETAILED DISCLOSURE OF THE INVENTION

The present invention discloses an antigen based vaccine against malaria comprising a fusion protein derived from *Plasmodium falciparum* Glutamate-rich protein (GLURP) genetically coupled to at least one other *Plasmodium falciparum* derived protein or homologues hereof.

A preferred embodiment of the invention is a vaccine where the protein genetically coupled to GLURP is derived from the Merozoite surface protein 3 (MSP3) from *Plasmodium falciparum* said fusion protein preferably having the amino acid sequence shown in SEQ ID NO 1.

In another embodiment the vaccine comprises SEQ ID NO 1 and further immunogenic epitopes of a protein derived from *Plasmodium falciparum*.

Also disclosed is the fusion protein as such with the amino acid sequence shown in SEQ ID NO. 1 and a fusion protein further comprising one or more immunogenic epitopes of one or more proteins derived from *Plasmodium falciparum*, such as CS, MSP1, MSP2, MSP4, MSP5, MSP6, AMA1, Pf155/RESA, RAP1, EBA-175, pfEMP1, EXP1, LSA1, LSA3, Pf25, Pf45/48, Pf230, Pf27, Pf16, or Pf28 is suggested.

The present invention also regards the preparation of above mentioned fusion protein from a recombinant bacteria, e.g. *Lactococcus*.

In another aspect, the invention relates a nucleic acid encoding the above mentioned fusion protein and the use of said nucleic acid for preparing a vaccine. A preferred embodiment of a nucleic acid used for a vaccine is the sequence as shown in SEQ ID NO 2.

In still another embodiment the vaccine comprises a recombinant BCG containing a nucleic acid sequence encoding above mentioned fusion protein.

Since vaccines based on GLURP and MSP3 induce the same type of immune responses i.e. high levels of cytophilic antibodies and possibly complement each other as targets for the immune system, the respective $GLURP_{25-500}$ and $MSP3_{212-382}$ regions were introduced together as a recombinant hybrid in *Lactococcus lactis* in a novel gene expression system, which is based on the pH and growth phase regulated promoter, P170, from *L. lactis* (7, 23, 33, 56). This gene expression system offers a simple fermentation procedure, which has been developed specifically for the P170 promoter. *L. lactis* was chosen as expression host because i) it is a well characterized industrial generally recognized as safe (GRAS) microorganism, best known for its use in the production of fermented dairy products, ii) it can be grown in a defined synthetic medium, iii) recombinant proteins may be secreted into the culture supernatant, from where they can be easily purified, iv) it does not produce toxic substances.

The N-terminal region of GLURP and the C-terminal region of MSP3 have now been produced in a chimeric fusion protein, as a hybrid protein, using *L. lactis*.

The immunogenicity of the hybrid protein has been studied in mice with Montanide (Seppic) used as the adjuvant. Montanide was used in recent clinical trials with long synthetic peptides derived from GLURP and MSP3, respectively. Immunizations with the hybrid protein consistently generated a stronger antibody response against the individual GLURP and MSP3 domains than a mixture of the two molecules.

The difference was most pronounced for the MSP3-specific antibody response suggesting that T cell epitopes located in the GLURP R0-region provide help for B-cell epitopes in the MSP3 region. This is a surprising ability of the GLURP antigen which can be used with other malarial antigens also.

In contrast, when the animals were injected with a mixture of GLURP and MSP3, individual mice tended to mount a predominant antibody response against either molecule. In some animals GLURP was immune dominant whereas in other animals MSP3 was the dominant immunogen.

The hybrid was also more effectively recognized by naturally occurring IgG antibodies in clinically immune African adults than the individual antigens.

The GLURP-MSP3 hybrid protein therefore has four major advantages compared to the individual GLURP and MSP3 molecules:

i) it is more immunogenic than any combination of the individual molecules,
ii) it generates a strong immune response against both GLURP and MSP3,
iii) it allows testing of both GLURP and MSP3 in a single clinical trial,
iv) it is predicted to be as safe as the individual molecules, since pre-clinical testing in mice and in non-human primates has shown that it does not contain neo-epitopes in the fusion junction between GLURP and MSP3.

Other identified antigens from *P. falciparum* suitable as a fusion partner to the GLURP antigen are CS, MSP1, MSP2, MSP4, MSP5, MSP6, AMA1, Pf155/RESA, RAP1, EBA-175, pfEMP1, EXP1, LSA1, LSA3, Pf25, Pf45/48, Pf230, Pf27, Pf16, or Pf28.

DEFINITIONS

Fusion Proteins

A recombinant fusion protein is encoded by a nucleotide sequence, which is obtained by genetically joining nucleotide sequences derived from different regions of one gene and/or by joining nucleotide sequences derived from two or more separate genes. These nucleotide sequences may be derived from *P. falciparum*, but they may also be derived from other organisms, the plasmids used for the cloning procedures or from other nucleotide sequences.

Immunogenic Fragment or Epitope

An immunogenic fragment or epitope is defined as a part of the protein that induces an immune response in a biological sample or an individual currently or previously infected with a microorganism such as malaria.

The immune response may be monitored by one of the following methods:

An in vitro cellular response is determined by release of a relevant cytokine such as IFN-γ, from lymphocytes withdrawn from an animal or human being currently or previously infected with malaria, or by detection of proliferation of these T cells. The induction being performed by the addition of the polypeptide or the immunogenic portion to a suspension comprising from $1\times10^5$ cells to $3\times10^5$ cells per well. The cells being isolated from either the blood, the spleen, the liver or the lung and the addition of the polypeptide or the immunogenic portion resulting in a concentration of not more than 20 µg per ml suspension and the stimulation being performed from two to five days. For monitoring cell proliferation the cells are pulsed with radioactive labeled Thymidine and after 16-22 hours of incubation detecting the proliferation by liquid scintillation counting. A positive response being a response more than background plus two standard deviations. The release of IFN-γ can be determined by the ELISA method, which is well known to a person skilled in the art. A positive response being a response more than background plus two standard deviations. Other cytokines than IFN-γ could be relevant when monitoring the immunological response to the polypeptide, such as IL-12, TNF-α, IL-4, IL-5, IL-10, IL-6, TGF-β. Another and more sensitive method for determining the presence of a cytokine (e.g. IFN-γ) is the ELISPOT method where the cells isolated from either the blood, the spleen, the liver or the lung are diluted to a concentration of preferable of 1 to $4\times10^6$ cells/ml and incubated for 18-22 hrs in the presence of the polypeptide or the immunogenic portion resulting in a concentration of not more than 20 µg per ml. The cell suspensions are hereafter diluted to 1 to $2\times10^6$/ml and transferred to Maxisorp plates coated with anti-IFN-γ and incubated for preferably 4 to 16 hours. The IFN-γ producing cells are determined by the use of labelled secondary anti-IFN-γ antibody and a relevant substrate giving rise to spots, which can be enumerated using a dissection microscope. It is also a possibility to determine the presence of mRNA coding for the relevant cytokine by the use of the PCR technique. Usually one or more cytokines will be measured utilizing for example the PCR, ELISPOT or ELISA. It will be appreciated by a person skilled in the art that a significant increase or decrease in the amount of any of these cytokines induced by a specific polypeptide can be used in evaluation of the immunological activity of the polypeptide.

An in vitro cellular response may also be determined by the use of T cell lines derived from an immune individual or a malaria infected person where the T cell lines have been driven with either live *P. falciparum*, extracts from the parasite or culture filtrate for 10 to 20 days with the addition of IL-2. The induction being performed by addition of not more than 20 µg polypeptide per ml suspension to the T cell lines containing from $1\times10^5$ cells to $3\times10^5$ cells per well and incubation being performed from two to six days. The induction of IFN-γ or release of another relevant cytokine is detected by ELISA. The stimulation of T cells can also be monitored by detecting cell proliferation using radioactively labeled Thymidine as described above. For both assays a positive response being a response more than background plus two standard deviations.

An in vivo cellular response which may be determined as a positive DTH response after intradermal injection or local application patch of at most 100 µg of the polypeptide or the immunogenic portion to an individual who is clinically or subclinically infected with *P. falciparum*, a positive response having a diameter of at least 5 mm 72-96 hours after the injection or application.

An in vitro humoral response is determined by a specific antibody response in an immune or infected individual. The presence of antibodies may be determined by an ELISA technique or a Western blot where the polypeptide or the immunogenic portion is absorbed to either a nitrocellulose membrane or a polystyrene surface. The serum is preferably diluted in PBS from 1:10 to 1:100 and added to the absorbed polypeptide and the incubation being performed from 1 to 12 hours. By the use of labeled secondary antibodies the presence of specific antibodies can be determined by measuring the OD e.g. by ELISA where a positive response is a response of more than background plus two standard deviations or alternatively a visual response in a Western blot.

Another relevant parameter is measurement of the protection in animal models induced after vaccination with the polypeptide in an adjuvant or after DNA vaccination. Suitable animal models include primates, guinea pigs or mice, which are challenged with an infection. Readout for induced protection could be decrease of the parasite density compared to non-vaccinated animals, prolonged survival times compared to non-vaccinated animals and diminished weight loss compared to non-vaccinated animals.

Homologue Protein

Homology is defined as an analogue or variant of the fusion protein of the present invention. The fusion protein is characterised by specific amino acids and is encoded by specific nucleic acid sequences. It will be understood that such sequences include analogues and variants produced by recombinant or synthetic methods wherein such polypeptide sequences have been modified by substitution, insertion, addition or deletion of one or more amino acid residues in the recombinant polypeptide and still be immunogenic in any of the biological assays described herein. Substitutions are preferably "conservative". Substitutions are preferably silent substitutions in the codon usage which will not lead to any change in the amino acid sequence, but may be introduced to enhance the expression of the protein. These are defined according to the following table. Amino acids in the same block in the second column and preferably in the same line in the third column may be substituted for each other. The amino acids in the third column are indicated in one-letter code.

| ALIPHATIC | Non-polar | GAP |
|---|---|---|
|  |  | ILV |
|  | Polar-uncharged | CSTM |
|  |  | NQ |
|  | Polar-charged | DE |
|  |  | KR |
| AROMATIC |  | HFWY |

Vaccine, Protein

The invention pertains to a vaccine composition comprising a fusion protein according to the invention. In order to ensure optimum performance of such a vaccine composition it is preferred that it comprises an immunologically and pharmaceutically acceptable carrier, vehicle or adjuvant.

An effective vaccine, wherein a protein of the invention is recognized by the animal, will in an animal model be able to decrease parasite load in blood and target organs, prolong survival times and/or diminish weight loss after challenge with a malarial parasite, compared to non-vaccinated animals Furthermore, the fusion protein of the invention may be coupled to a carbohydrate or a lipid moiety, e.g. a carrier, or a modified in other ways, e.g. being acetylated.

When produced in a microorganism the fusion protein of the invention will normally not be acetylated if no special measures are taken. The acetylation may be advantageous as acetylated polypeptides may be more stable in cell, blood or body and tissue fluids. Furthermore, the acetylation may confer the polypeptide with a structure and confirmation which mimics the structure and confirmation of the native *P. falciparum* antigen.

Suitable carriers are selected from the group consisting of a polymer to which the polypeptide(s) is/are bound by hydrophobic non-covalent interaction, such as a plastic, e.g. polystyrene, or a polymer to which the polypeptide(s) is/are covalently bound, such as a polysaccharide, or a polypeptide, e.g. bovine serum albumin, ovalbumin or keyhole limpet haemocyanin. Suitable vehicles are selected from the group consisting of a diluent and a suspending agent. The adjuvant is preferably selected from the group consisting of dimethyldioctadecylammonium bromide (DDA), Quil A, poly I:C, aluminium hydroxide, Freund's incomplete adjuvant, IFN-γ, IL-2, IL-12, monophosphoryl lipid A (MPL), Treholose Dimycolate (TDM), Trehalose Dibehenate and muramyl dipeptide (MDP).

Preparation of vaccines which contain peptide sequences as active ingredients is generally well understood in the art, as exemplified by U.S. Pat. Nos. 4,608,251; 4,601,903; 4,599,231 and 4,599,230, all incorporated herein by reference.

Other methods of achieving adjuvant effect for the vaccine include use of agents such as aluminum hydroxide or phosphate (alum), synthetic polymers of sugars (Carbopol), aggregation of the protein in the vaccine by heat treatment, aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. Other possibilities involve the use of immune modulating substances such as cytokines or synthetic IFN-γ inducers such as poly I:C in combination with the above-mentioned adjuvants.

Another interesting possibility for achieving adjuvant effect is to employ the technique described in Gosselin et al, 1992 (19). In brief, a relevant antigen such as an antigen of the present invention can be conjugated to an antibody (or antigen binding antibody fragment) against the Fcγ receptors on monocytes/macrophages.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 μg to 1000 μg, such as in the range from about 1 μg to 300 μg, and especially in the range from about 10 μg to 50 μg. Suitable regimens for initial administration and booster shots are also variable but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the age of the person to be vaccinated and, to a lesser degree, the size of the person to be vaccinated.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and advantageously contain 10-95% of active ingredient, preferably 25-70%.

In many instances, it will be necessary to have multiple administrations of the vaccine. Especially, vaccines can be administered to prevent an infection with malaria and/or to treat established malarial infection. When administered to prevent an infection, the vaccine is given prophylactically, before definitive clinical signs or symptoms of an infection are present.

Due to genetic variation, different individuals may react with immune responses of varying strength to the same protein. Therefore, the vaccine according to the invention may comprise several different proteins in order to increase the immune response. The vaccine may comprise two or more polypeptides or immunogenic portions, where all of the proteins are as defined above, or some but not all of the peptides may be derived from P. falciparum or other microorganisms. In the latter example, the polypeptides not necessarily fulfilling the criteria set forth above for polypeptides may either act due to their own immunogenicity or merely act as adjuvants.

The vaccine may comprise 1-20, such as 2-20 or even 3-20 different proteins or fusion proteins, such as 3-10 different proteins or fusion proteins.

The invention also pertains to a method for immunising an animal, including a human being, against malaria caused by e.g. P. falciparum, comprising administering to the animal the fusion protein of the invention, or a vaccine composition of the invention as described above, or a living vaccine described below.

The invention also pertains to a method for producing an immunologic composition according to the invention, the method comprising preparing, synthesising or isolating a fusion protein according to the invention, and solubilizing or dispersing the fusion protein in a medium for a vaccine, and optionally adding other antigens and/or a carrier, vehicle and/or adjuvant substance.

Another aspect of the invention is producing the hybrid protein of the invention in a recombinant microorganism which, besides expressing the DNA sequence encoding the present hybrid protein, additionally expresses one or more antigens having a therapeutic or protective effect against another disease than malaria, e.g. tuberculosis. These other antigens can be expressed as separate antigens or as fused to the hybrid protein of the present invention. Examples of other antigens effective against Tb are ESAT6, CFP7, CFP10, CFP29, ORF2c, TB13, MPT59, α-crystalline, Rv0285 and hybrids hereof, but the concept is not limited to TB or antigens against TB alone.

Vaccine DNA

The nucleic acid fragments of the invention may be used for effecting in vivo expression of antigens, i.e. the nucleic acid fragments may be used in so-called DNA vaccines as reviewed in Ulmer et al 1993, which is included by reference.

Hence, the invention also relates to a vaccine comprising a nucleic acid fragment according to the invention, the vaccine effecting in vivo expression of antigen by an animal, including a human being, to whom the vaccine has been administered, the amount of expressed antigen being effective to confer substantially increased resistance to infections caused by P. falciparum in an animal, including a human being.

The efficacy of such a DNA vaccine can possibly be enhanced by administering the gene encoding the expression product together with a DNA fragment encoding a polypeptide which has the capability of modulating an immune response.

Live Recombinant Vaccines

One possibility for effectively activating a cellular immune response for a vaccine can be achieved by expressing the relevant antigen in a vaccine in a non-pathogenic microorganism or virus. Well-known examples of such microorganisms are *Mycobacterium bovis* BCG, *Salmonella* and *Pseudomona* and examples of viruses are Vaccinia Virus and Adenovirus.

Therefore, another important aspect of the present invention is an additional quality of the living BCG vaccine presently available, wherein one or more copies of a DNA sequence encoding one or more fusion proteins as defined above has been incorporated into the genome of the microorganism in a manner allowing the micro-organism to express and secrete the protein. The incorporation of more than one copy of a nucleotide sequence of the invention is contemplated to enhance the immune response.

Another aspect of the invention is a non-pathogenic microorganism, such as e.g. *L. lactis* or BCG, expressing the DNA sequence encoding one or more fusion proteins as defined above and additionally expressing one or more antigens having a therapeutic or protective effect against a disease different from malaria, such as e.g. tuberculosis caused by *Mycobacterium tuberculosis*. These other antigens can be expressed as separate antigens or as fused to the hybrid protein of the present invention. Examples of other antigens effective against Tb (identified by their Sanger database accession number) are Rv3875 (ESAT6), Rv1886c (Ag85B), Rv0288 (CFP7), Rv3874 (CFP10), Rv0798c (CFP29), Rv2031c (α-crystalline) and Rv0285 or fragments or hybrids hereof most preferable the ESAT6-Ag85B hybrid, but the concept is not limited to TB or antigens against TB alone.

The effect of such a DNA-vaccine can possibly be enhanced by administering the gene encoding the expression product together with a DNA fragment encoding a polypeptide which has the capability of modulating an immune response. For instance, a gene encoding lymphokine precursors or lymphokines (e.g. INF-γ, IL-2, IL-12) could be administered together with the gene encoding the immunogenic fusion protein, either by administering two separate DNA fragments or by administering both DNA fragments included in the same vector.

Another possibility is to integrate the DNA encoding the polypeptide according to the invention in an attenuated virus such as the vaccinia virus or Adenovirus (40). The recombinant vaccinia virus is able to replicate within the cytoplasma of the infected host cell and the protein of interest can therefore induce an immune response, which is envisioned to induce protection against malaria.

Therapeutic Vaccine

The invention also relates to the use of a fusion protein or nucleic acid of the invention for use as therapeutic vaccines as have been described in the literature exemplified by D. Lowry (Lowry et al 1999). Antigens with therapeutic properties may be identified based on their ability to diminish the severity of malarial infection in experimental animals or prevent reactivation of previous infection, when administered as a vaccine. The composition used for therapeutic vaccines can be prepared as described above for vaccines.

LEGENDS TO FIGURES

FIG. 1. Schematic representation pf pPSM1013 and pAMJ328 and the expression constructs used in *L. lactis*. The position of vector encoded restriction sites mentioned in the text, promoter P170, Shine-Dalgarno sequence (SD), and 310mut2 signal peptide are indicated. The signal peptidase is predicted to cleave between amino acid no. 32 and 33, thus leaving Ala-Glu residues in the N-terminal end of the mature recombinant proteins. The nucleotide numbering of glurp and MSP3 was relative to A in the ATG codon of M59706 and L07944, respectively.

Figure 2A:
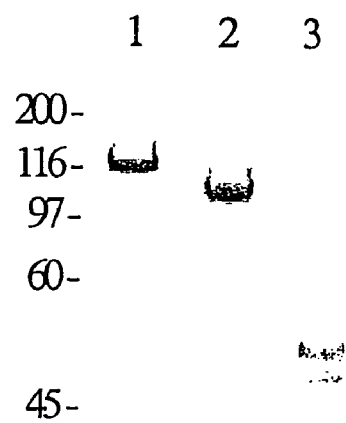
Figure 2A:
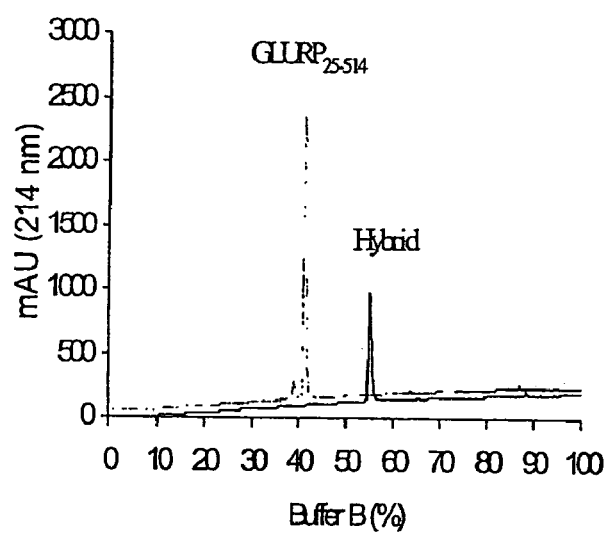

FIG. 2. (A) Coomassie blue-stained 12.5% polyacrylamide gel of purified GLURP-MSP3 fusion protein (lane 1), GLURP$_{25-514}$ (lane 2), and MSP3$_{212-380}$ (lane 3) produced in *L. lactis* MG1363. (B) HPLC analysis on a C4 column of the GLURP-MSP3 hybrid protein (SEQ ID NO: 1) and GLURP$_{25-514}$, (SEQ ID NO: 1), respectively. The sizes (in kilodaltons) of the molecular mass markers are indicated. (C) Deduced amino acid sequences and peptide mapping of GLURP-MSP3 hybrid and GLURP$_{25-514}$. The first four amino acids (Ala-Glu-Arg-Ser) (residues 1-4 of SEQ ID NO: 1) of the GLURP-MSP3 hybrid are derived from the cloning vector pSM1013. Samples for peptide mass mapping for were cut out of a coomassie stained SDS-PAGE gel. Half a 35 band (approx. 1 µg protein) was washed, dried, reduced and alkylated with iodoacetamide before being digested overnight by modified trypsin (PROMEGA®, USA), essentially as described (44). The supernatant of the digest was applied to GELOADER® tips (EPPENDORFF®, Germany) packed with POROS® 20 R2 reversed phase material (PERSEPTIVE®, USA) and eluted with 0.8 µl of alpha-cyanohydroxy-cinnamic acid (20 µg/µl in 70% acetonitrile/30% water) directly onto the MALDI target (28). Analysis was carried out on a PerSeptive Voyager STR (PERSEPTIVE®, USA) operated in the reflector mode and the results were analyzed in GPMAW ver. 5.02 (LIGHTHOUSE DATA®, Denmark). Sequences covered by peptides in the MALDI-TOF spectra are underlined and the percentage of total coverage of sequencing is indicated.

Figure 3:
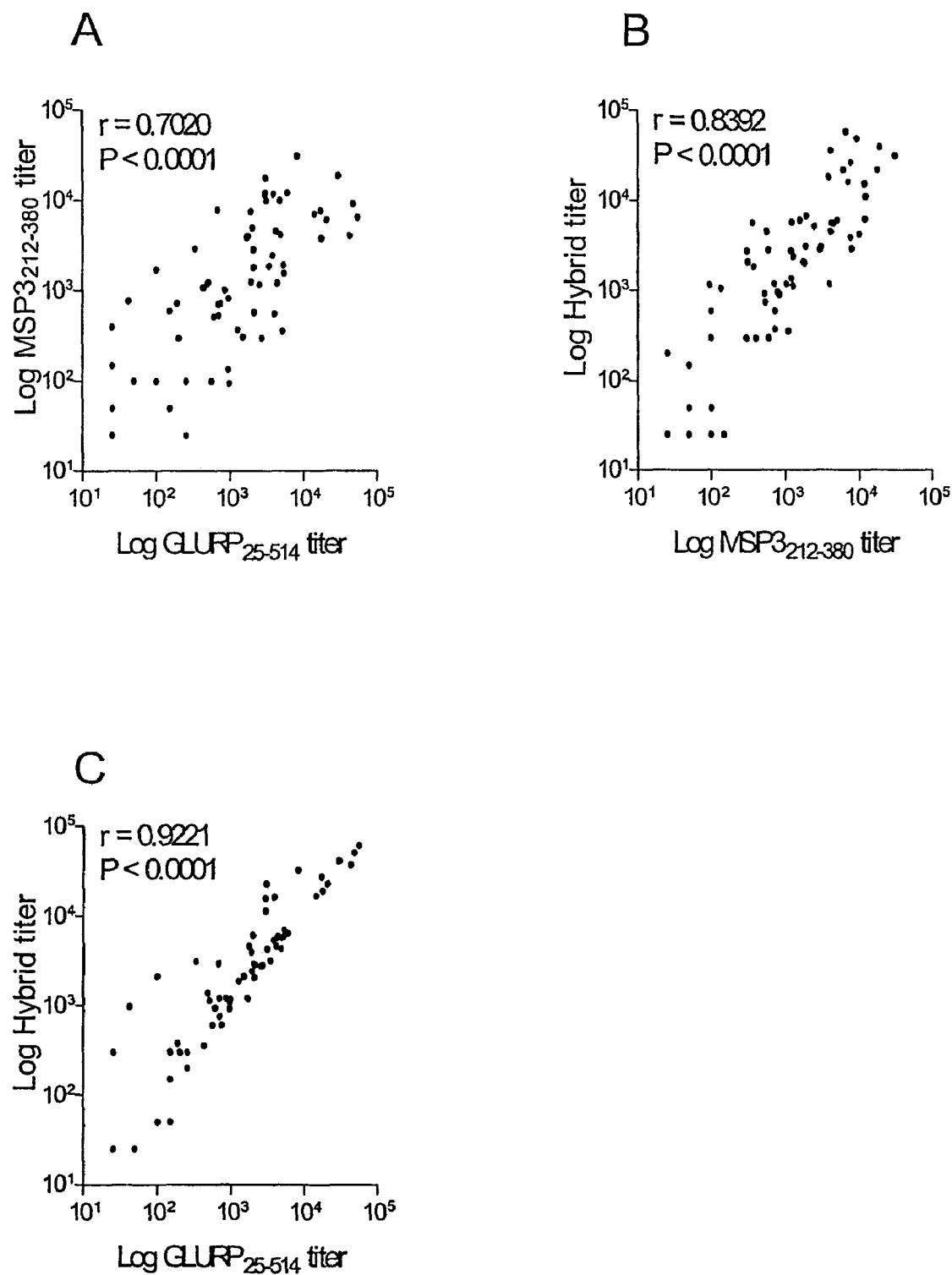

FIG. 3. Patterns of IgG antibody responses to pairs of GLURP and MSP3 derived antigens in 71 plasma samples from adult Liberians clinically immune to malaria. The coefficient of correlation and P value are provided in each panel.

Figure 4:
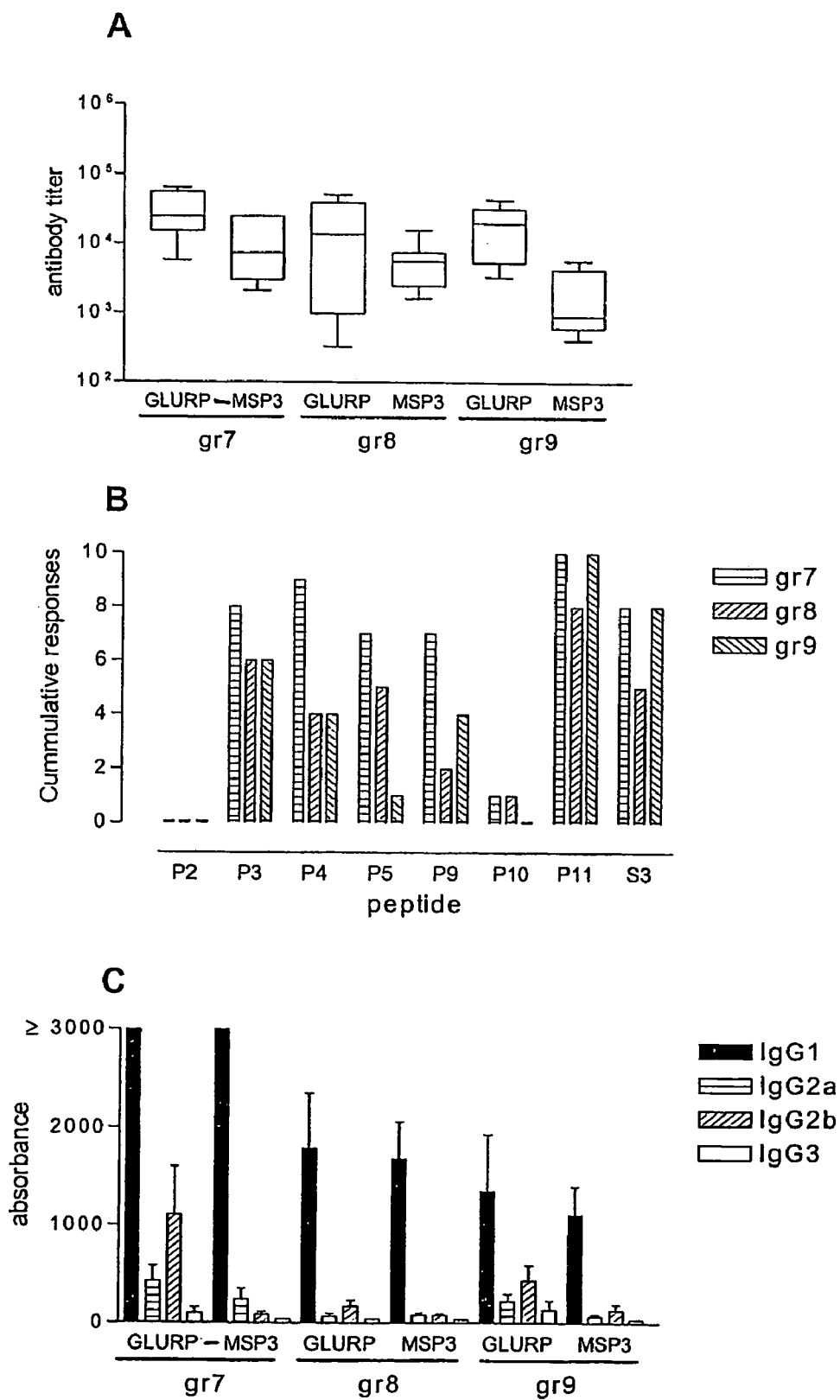

FIG. 4. Antibody responses in mice. Groups of 10 mice were immunized with the hybrid (gr7), a mixture of GLURP and MSP3 in one syringe (gr8), or with GLURP and MSP3 in separate syringes at different sites (gr9). (A) Day 35 plasma samples were tested for antibody reactivity on ELISA plates coated with GLURP$_{25-514}$ or MSP3$_{212-3}$. Box plots show medians, 25$^{th}$, and 75$^{th}$ percentiles and whiskers show the range of the data. (B) Cumulative responses of mouse sera with 8 peptides representing GLURP B-cell epitopes (51) and (C) isotype response of mice for which results are presented in panel A. Each vertical bar represents the mean absorbance (±SEM) in GLURP- and MSP3-specific ELISAs.

Figure 5:
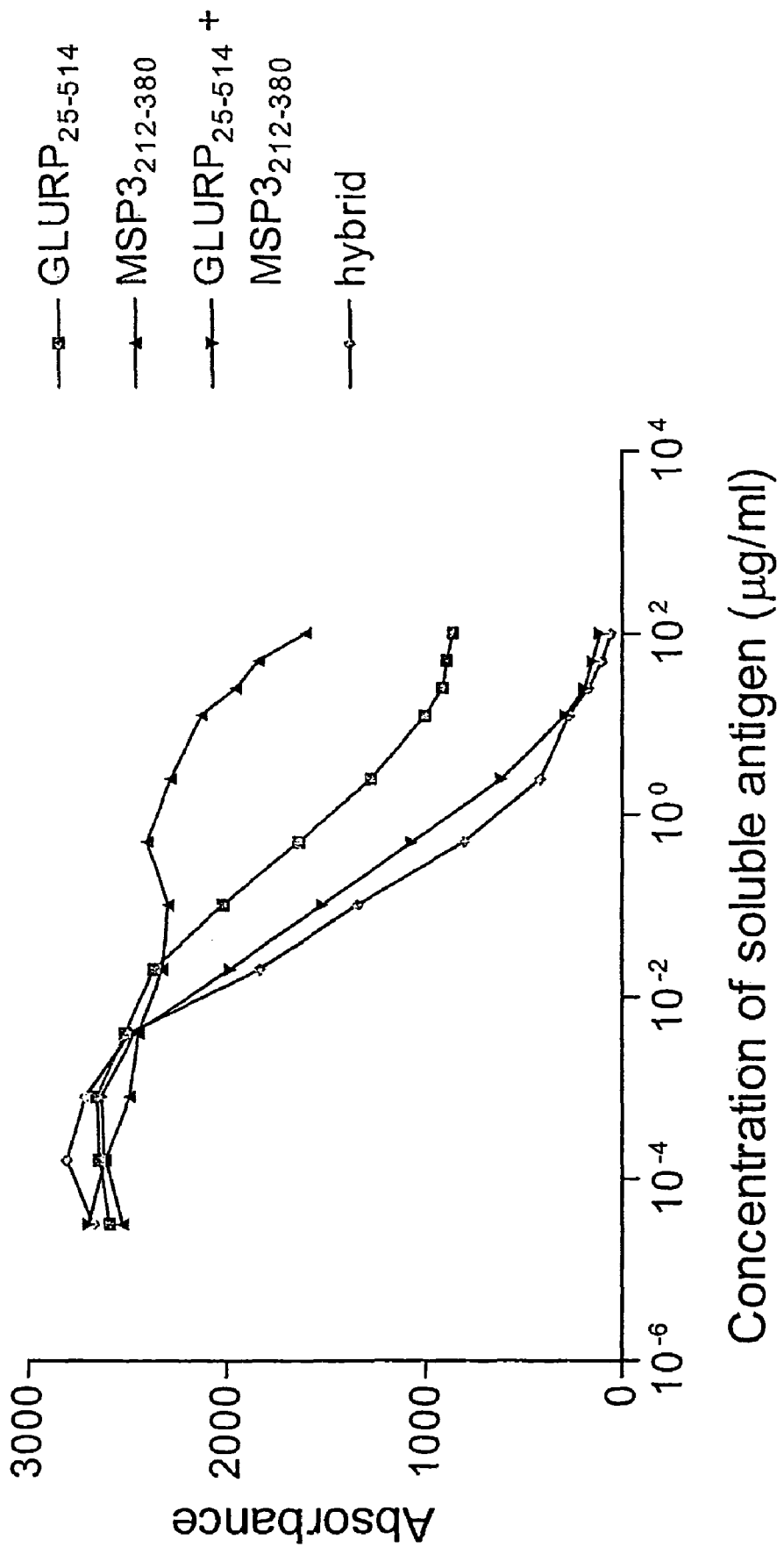

FIG. 5. The hybrid contains only GLURP and MSP3 derived B-cell epitopes. A pool of plasma from mice immunized with the hybrid was pre-incubated with GLURP, MSP3, a mixture of GLURP and MSP3 or the hybrid at the indicated concentrations before being added to ELISA coated with the hybrid. Prior incubation with a mixture of GLURP and MSP3 or the hybrid completely inhibited Ig antibody binding to the hybrid.

Figure 6:
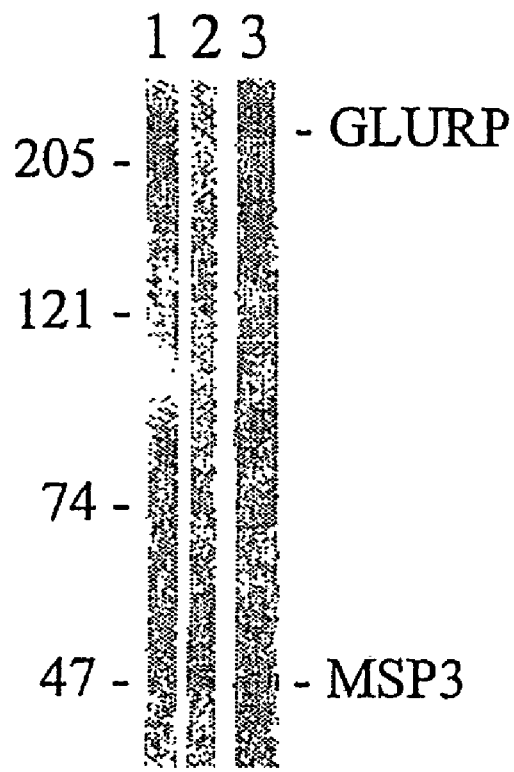

FIG. 6. Immunoblot analysis of *P. falciparum* NF54. A whole cell extract was separated on a 7.5% polyacrylamide gel and subjected to immunoblotting with plasma from mice immunized with GLURP$_{25-514}$ (lane 1), MSP3$_{212-380}$ (lane 2) and GLURP-MSP3 hybrid (lane 3). The sizes (in kilodaltons) of the molecular mass markers are indicated.

EXAMPLE

Example 1

Materials and methods

Bacterial strains, plasmids and growth conditions. *E. coli* DH10B (K-12, F$^-$ mcrA Δ(mrr-hsdRMS-mcrBC) Φ80dlacZ Δm15 ΔlacX74 deoRrecA1 endA1 araD139 Δ(ara, leu) 7697galUgalK λ$^-$ rpsL nupG) (LIFE TECHNOLOGIES®) containing the indicated plasmids was grown in Luria broth (LB) supplemented with erythromycin (200 µg/ml). *L. lactis* MG1363 (17) containing the indicated plasmids was grown in either M17 broth (DIFCO® Ltd.) with 0.5% (wt/vol) glucose or an enhanced synthetic amino acid (SA) medium named 3×SA IV medium (24) supplemented with 1 µg/ml of erythromycin. Solidified LB or M17 media was supplemented with 200 or 1 µg/ml of erythromycin, respectively. The vector, pPSM1013 (FIG. 1), is a high-copy number expression plasmid based on the pAMp1 replicon (46) containing unique restriction sites allowing the construction of in-frame fusions with an optimized secretion signal-peptide sequence, SP310mut2 (Ravn, P., Arnau, J., Madsen, S. M., Vrang, A., and Israelsen, H. unpublished). The mRNA for the peptide is translated from a plasmid-encoded translational start site and transcribed from the pH and growth phase inducible *L. lactis* promoter, P170 (7, 23, 33). There is essentially no transcription from the P170 promoter at pH values of 7 or more. However, the transcription is induced in the transition to stationary phase at pH values below 6.5. Plasmid pAMJ328 is derived from pPSM1013 by deleting all lacZ regulatory sequences to avoid transcription from the lac promoter and by creating a new cloning region devoid of the signal peptide (32).

Construction of plasmids expressing GLURP and MSP3 in *L. lactis*. All plasmids were constructed in *E. coli* DH10B and transformed into *L. lactis* MG1363 by electroporation as described (22). All plasmid constructions were verified by DNA sequencing. pMST73. The non-repeat region of FVO glurp was amplified with the primers 5'-<u>CCCAGATCT</u> ACA AGT GAG AAT AGA AAT AAA C (SEQ ID NO: 3) [nucleotides 79 to 100] (counting from A in the ATG start codon of M59706) and 5'-<u>CCCAGATCT</u> TGC TTC ATG CTC GCT TTT TT CCG AT (SEQ ID NO: 4) [nucleotides 1475 to 1500]; digested with BglII, and the resulting DNA fragment was cloned into BglII digested pPSM1013.

pKBR5. pMST73 plasmid was digested with BamHI and SalI, and the resulting DNA fragment containing the glurp insert was cloned into BamHI-SalI digested pAMJ328.

pKBR7. The non-repeat region of F32 glurp was amplified with the primers 5'-<u>AAGTAGATCT</u>AC TAA TAC AAG TGA GAA TAG AAA TAA AC (SEQ ID NO: 5) [nucleotides 73 to 100], and 5'-<u>GTTCAGATCT</u>TT ATT CAT GAT GGC CTT CTA GC (SEQ ID NO: 6) [nucleotides 1519 to 1542]; the resulting DNA fragment digested with BglII and cloned into BglII digested pPSM1013.

pKBR8. Plasmid pKBR7 was digested with BamHI and SalI, and the glurp insert was cloned into BamHI-SalI digested pAMJ328.

pKBR9. The C-terminal region of F32 MSP3 was amplified with the primers 5'-CCC <u>AGATCT</u> AAA GCA AAA GAA GCT TCT AGT TAT (SEQ ID NO: 7) [nucleotides 628 to 651] and 5'-ATT <u>AGATCT</u> CAT TTA ATG ATT TTT AAA ATA TTT GGA TA (SEQ ID NO: 8), [nucleotides 1118 to 1140] (counting from A in the ATG start codon of L07944); the resulting DNA fragment was digested with BglII and cloned into BglII digested pPSM1013. This MSP3 region is identical to that of the FC27 allele (Accession number L07944) except for the following residues at variable positions in MSP3: 735 (T C) and 948 (A G).

pKBR10. Plasmid pKBR9 was digested with BamHI and SalI, and the MSP3 insert was cloned into BamHI-SalI digested pAMJ328.

pKBR11. The BglII-fragment of pKBR9 was cloned into pKBR5 digested partially with BglII yielding an in frame fusion between glurp$_{79-1500}$ and MSP3$_{628-1140}$. This hybrid molecule corresponds to the F32 allele except for the following residues at variable positions in GLURP: Leu-50, Asn-53, Glu-65, Asp-129, Glu-224, Pro-500.

Fermentation. Fermentation of L. lactis MG1363, containing plasmid pKBR8 (GLURP), pKBR10 (MSP3) or pKBR11 (GLURP-MSP3 hybrid), was carried out in 1 L of 3×SA IV-media supplemented with erythromycin (1 µg/ml), yeast-extract (0.5%) 25 and glucose (1.5%) in 2 L fermentors at 30° C. The starting pH of the culture medium was adjusted to 7.4. Since L. lactis MG1363 produces lactic acid during the growth, pH is declining as cell density increases. After approximately 3 hours of growth, pH was reduced to 6 and this level was maintained by a pH-controlled intake of 2 M KOH for another 8 hours until the cell density was approximately $OD_{600}$=8. A 50% glucose solution was added in parallel with the base since this tends to increase the bacterial yield. Bacterial cells were removed from the culture-supernatant (containing exported protein) by ultrafiltration with a Pellicon 2 DURAPORE® filter (PVDF, 0.22 µm, 0.1 m2) (MILLIPORE®). Culture-supernatants were either used immediately or stored at −20° C.

Purification of recombinant proteins. A purification strategy was developed for the recombinant GLURP, MSP3 and hybrid molecules. Cell-free culture-supernatants were concentrated on a MILLIPORE® Labscale TFF System installed with a Pellicon XL Biomax 8 filter (Polypropylene-membrane, 50000 Da, 50 cm2) and concentrates were buffer exchanged to 20 mM Bis-Tris (pH 6.4) on a Sephadex G-25 column (C26/40, 170 ml). Recombinant proteins were first purified on a 5 ml HITRAP™ Q SEPHAROSE™ High Performance (PHARMACIA® Biotech) column by applying a gradient of 0 to 1 M NaCl in column buffer at a flow-rate of 1 ml/min. Fractions (2 ml) containing the desired recombinant protein were pooled and dialyzed against 20 mM Bis-Tris (pH 6.4) and applied to a 5 ml HiTrap SP Sepharose High Performance (PHARMACIA® Biotech) column. The recombinant protein was eluted by a gradient of 0 to 1 M NaCl in column buffer. GLURP and MSP3 were eluted in single peaks whereas the hybrid was eluted in two peaks. Fractions (2 ml) containing the desired peaks were pooled and adjusted to 1 M $(NH_4)_2SO_4$ and further purified on a 5 ml Phenyl SEPHAROSE™ High Performance (PHARMACIA® Biotech) by applying a gradient of 1 to 0 M $(NH_4)_2SO_4$ in 20 mM Bis-Tris (pH 6.4) at a flow-rate of 1 ml/min. Analysis of all fractions was performed by SDS-PAGE. Protein concentrations were measured by the BCA™ protein assay (PIERCE®, Rockford, Ill., USA).

Immunization and purification of mouse IgG. Thirty BALBc/CF1 BALBc/CFI mice (27) female mice (7 to 10 weeks of age) were randomly assigned to three groups. Two groups were immunized with 20 µg of GLURP$_{27-500}$-MSP3$_{212-380}$ hybrid (gr7), or with a mixture of 15 µg GLURP$_{25-512}$ and 5 µg MSP3$_{212-380}$ (gr8) by subcutaneous injections at the base of the tail, respectively; and the third group (gr9) received 15 µg GLURP$_{25-512}$ injected at the base of the tail and 5 µg MSP3$_{212-380}$ injected in the shoulder. All immunogens were emulsified in MONTANIDE™, incomplete Freund's adjuvant, and each mouse received three injections at 2-week intervals and was bleed on days 0, 14, 28 and 35. Total IgG was purified by $(NH_4)_2SO_4$ precipitation and subsequent purification on DEAE-columns from pooled serum samples taken on day 35 from animals in the groups gr7, 8, and 9 and from pooled day 0 samples.

ELISA and serum samples. Enzyme-linked immunosorbent assays (ELISAs) were performed as previously described in detail (54). The coating concentrations of GLURP$_{25-512}$, MSP3$_{212-380}$, and GLURP$_{27-500}$-MSP3$_{212-380}$ were 0.5, 1.0 and 0.5 µg/ml respectively. Serial dilutions of plasma from Liberian adults clinically immune to malaria, Danish donors never exposed to malaria (51), and mice were tested on ELISA plates coated with either antigen and the absorbance values were plotted against the plasma dilutions. In order to compare anti-hybrid antibody responses with the respective anti-GLURP and anti-MSP3 antibody responses in different plasma samples the antibody titer was defined as the plasma dilution, which gives an absorbance value of A492=1000 in the parallel portion of the curves.

Competition ELISA assays. Recombinant GLURP$_{25-518}$ and MSP3$_{212-380}$ and a mixture of these two antigens were added at various concentrations ($3.2 \times 10^{-5}$ µg/ml to 100 µg/ml) to a pool of plasma from mice immunized with the GLURP-MSP3 hybrid diluted in 1.25% (w/v) milk powder in PBS. The plasma dilution used was adjusted to give an absorbance (A492) of approximately 2500. The antigen-antibody mixtures were incubated overnight at 4° C. and subsequently the reactivity to GLURP-MSP3 hybrid coated ELISA plates was determined.

Indirect Immunofluorescent Antibody (IFA) test. IFA was performed as reported earlier (5). Briefly, a thin film of RBCs containing predominantly schizonts stages of P. falciparum NF54 were incubated with serial dilutions of purified mouse IgG in phosphate buffered saline (PBS pH 7.4) for 30 min at 37° C. in a humid chamber. After washing with PBS, mouse antibodies were revealed with Alexa Fluor conjugated goat anti-mouse IgG (Molecular probe, USA) diluted 1:300 in PBS. After washing the slide was examined under UV light. The endpoint titre was the highest dilution of the antibodies, which produce visible specific immunofluorescence.

RP-HPLC analysis of GLURP and GLURP-MSP3. Samples were analyzed on a HPLC system (Pharmacia, Sweden), using a Protein C4 column (VYDAC®, 214TP54, USA). Analysis was done in a Acetonitrile:$H_2$O:TFA buffer system. Purified samples were diluted 1:2 in A-buffer ($H_2$O+ 0,1% (w/v) TFA) and applied on the column, elution was done using a linear gradient 0-80% B-buffer (80% Acetonitrile+0.1% (w/v) TFA) over 20 column volumes. Elution was monitored by UV-Abs. 214 nm. Peaks were collected and vacuum dried on a HetoVac (Heto, Denmark) and kept on 4° C. until further experiments.

Maldi-Tof MS and ES-MS. Samples for peptide mass mapping for were cut out of a coomassie stained SDS-PAGE gel. Half a band (approx. 1 µg protein) was washed, dried, reduced and alkylated with iodoacetamide before being digested overnight by modified trypsin (PROMEGA®), essentially as described (44). The supernatant of the digest was applied to GELOADER® tips (EPPENDORFF®, Germany) packed with POROS® 20 R2 reversed phase material (PERSEPTIVE®, USA) and eluted with 0.8 µl of alpha-cyanohydroxycinnamic acid (20 µg/µl in 70% acetonitrile/30% water) directly onto the MALDI target (28). Analysis was carried out on a (PERSEPTIVE®, USA) operated in the reflector mode and the results were analyzed in GPMAW ver. 5.02 (LIGHTHOUSE DATA®, Denmark). Electrospray mass spectrometry of the intact protein was carried out on a fraction from RP-HPLC (approx. 20 µg protein). The sample was dried down and re-dissolved in 5% formic acid to a concentration of 20 pmol/µl before being analyzed on a MICROMASS® QTOF (Micromass MICROMASS®, UK) using a nanospray source.

Example 2

Expression of glurp and MSP3 in *L. lactis*

PCR fragments encoding the $glurp_{79-1500}$ and $MSP3_{628-1140}$ regions were cloned side by side thereby creating an in-frame fusion between a vector-encoded signal-peptide and a $GLURP_{27-500}$-$MSP3_{212-380}$ fusion protein (pKBR11, FIG. 1). This hybrid contains two additional amino acid residues created by joining these glurp and MSP3 fragments. For comparison, the individual $glurp_{73-1542}$ and $MSP3_{628-1140}$ fragments were also cloned (pKBR8 and pKBR10, FIG. 1). Plasmids were transformed into *L. lactis* MG1363 and the resulting strains were grown in fermentors as described in Materials and Methods. The pH of the growth medium was maintained at 6 to achieve optimal transcription from the P170 promoter (33). All three recombinant proteins were secreted into the culture supernatants from where they were purified by sequential ion exchange on HiTrap Q and SP Sepharose columns followed by hydrophobic interaction chromatography on Phenyl Sepharose. Subsequent SDS-PAGE showed that the plasmids pKBR11 (lane 1), pKBR8 (lane 2), and pKBR10 (lane 3) produced major products of 136, 100, and 36 kDa respectively (FIG. 2A). Additional lower molecular-mass bands were observed in the purified GLURP and MSP3 preparations. When analyzed by immunoblotting the smaller products in lanes 2 and 3 were specifically recognized, as were the full-length products, by antibodies to GLURP and MSP3 respectively, suggesting that they may result from incomplete translation of the mRNA and/or from protease cleavage of the primary protein products. A MALDI MS tryptic peptide map of the SDS-PAGE purified bands in lane 2 confirmed that this smaller molecular-mass protein is derived from $GLURP_{25-514}$ (data not shown). The purity of the $GLURP_{27-500}$-$MSP3_{212-380}$ and $GLURP_{25-514}$ preparations was assessed by HPLC as described in Materials and Methods. $GLURP_{27-500}$-$MSP3_{212-380}$ so and $GLURP_{25-514}$ gave single major peaks (FIG. 2B). The molecular masses of $GLURP_{27-500}$-$MSP3_{212-380}$ and $GLURP_{25-514}$ were 74950 and 56518 Da (±20 Da), respectively, as determined by ES MS. Assuming that the two recombinant proteins each contain the vector encoded amino acid residues, A-E-R-S, attached to their N-terminal ends (FIG. 1), these molecular weights corresponds well to the predicted values of 74939 and 56518, respectively. Thus, both $GLURP_{27-500}$-$MSP3_{212-380}$ and $GLURP_{25-514}$ recombinant proteins were intact and contained the predicted amino acid residues.

Example 3

Antigenicity of GLURP and MSP3 Produced in *L. lactis*

The antigenicity of the recombinant proteins was evaluated against plasma from 71 adults Liberians clinically immune to malaria (FIG. 3). Serial dilutions of all plasma samples were tested on separate plates coated with each recombinant protein and the antigen-specific titer was determined as the dilution giving an absorbance of 1000. As expected, different plasma contained different amounts of GLURP and MSP3-specific IgG antibodies (FIG. 3A). In general, hybrid-specific antibody titers exceeded those recorded with the individual $GLURP_{25-514}$ and MSP3 antigens (FIGS. 3B and C) suggesting that the hybrid molecule provides an adequate presentation of GLURP and MSP3 antigenic determinants, respectively.

Example 4

Immunogenicity of Recombinant GLURP and MSP3 Products

To determine whether the GLURP-MSP3 hybrid molecule is a superior immunogen compared to a mixture of the individual $GLURP_{25-514}$ and $MSP3_{212-380}$ molecules, groups of BALBc/CF1 mice were each immunized subcutaneously with the hybrid molecule in Montanide or with $GLURP_{25-514}$ and $MSP3_{212-380}$ combined in either one syringe or injected separately at two different sites. Following the third injection, day-35 sera were tested for IgG antibody reactivity against GLURP and MSP3, respectively. While the mean GLURP-ELISA titer is only marginally higher in the hybrid group than in the other two groups, mean MSP3-ELISA titer is 4.3-fold higher (Kruskal Wallis test, $P<0.004$) in the group receiving the hybrid compared to the group receiving $MSP3_{212-380}$ and $GLURP_{25-514}$ at two different sites (compare gr7 and gr9 in FIG. 4A). At the individual level, mice immunized with the hybrid reacted strongly with both GLURP and MSP3 domains whereas mice immunized with a combination of two molecules tended to mount a predominant antibody response against either GLURP or MSP3. The anti-hybrid IgG antibodies are mainly directed against the P3, P4, P11, and S3 peptides containing known epitopes for human antibodies (51); however peptides P5 and P9 which do not contain such epitopes were also recognized (FIG. 4B). Whereas the GLURP and MSP3-specific IgG subclass profiles are similar for all vaccine formulations (FIG. 4C), GLURP-specific IgG antibodies tends to use the Kappa light chain and MSP3-specific IgG antibodies tends to use the Lambda light chain. This difference in light chain was found for all GLURP or MSP3-specific antibodies whether raised against the hybrid or the mixtures of the individual molecules.

The specificity of mouse antibodies to the hybrid was also analyzed by competition-ELISA (FIG. 5). It appears that antibodies to the hybrid are purely GLURP and MSP3-specific, since a mixture of soluble $GLURP_{25-514}$ and $MSP3_{212-380}$ could completely inhibit the binding of anti-hybrid antibodies to immobilized $GLURP_{27-500}$-$MSP3_{212-380}$. Thus, the construction of a GLURP-MSP3 hybrid molecule has not created new B-cell epitopes in the overlapping area.

Example 5

Reactivity of Mouse Anti-GLURP and Anti-MSP3 Sera with Native GLURP and MSP3

The immunogenicity of the recombinant GLURP and MSP3 was also investigated by immunoblotting of parasite-derived proteins with sera from mice immunized with each of the three recombinant proteins, hybrid, $GLURP_{25-514}$ and $MSP3_{212-380}$, respectively. As demonstrated in FIG. 6, plasma from mice immunized with $GLURP_{25-514}$, MSP3$_{212-380}$, and the hybrid recognized polypeptides of approximately 220,000 Da (lane 1), 48,000 Da (lane 2), and both (lane 3), respectively.

Example 6

Antigen Competition Between GLURP and MSP3 Produced as Long Synthetic Peptides (SEQ ID NOS 9-10, Respectively)

Immunogens

The MSP3 and GLURP regions used were produced as long synthetic peptides:

```
MSP3 (LR55):  181-RKTKEYAEKA KNAYEKAKNA YQKANQAVLK
              AKEASSYDYI LGWEFGGGVP EHKKEENMLS
              HLYVSSKDKE NISKENDDVL DEKEEEAEET
              EEEELE 276.
              and
GLURP (LR67): 85 NVPSGL DIDDIPKESI FIQEDQEGQT
              HSELNPETSE HSKDLNNNGS KNESSDIISE
              NNKSNKVQNH FESLSDLELL ENSSQDNLDK
              DTISTEPFPN QKHKDLQQDL NDEPLEPFPT
              QIHKDYKEKN LIN-213.
```

Immunizations

Twenty BALBc female mice (7 to 10 weeks of age) were randomly assigned to four groups and immunized by subcutaneous injections with different combinations of MSP3 and GLURP:
1. group 110 was immunized with 5 µg of LR55,
2. group 111 was immunized with 5 µg of LR67,
3. group 112 was immunized with a mixture of 5 µg LR55+5 µg LR67 by subcutaneous injections at the base of the tail,
4. group 113 received 5 µg LR55 injected at the base of the tail and 5 µg LR67 injected in the shoulder.

All immunogens were emulsified in Montanide ISA720 and each mouse received three injections at 2-week intervals and was bleed on days 0, 14, 28 and 35.

ELISA

Serial dilutions of day 35 plasma samples were tested on ELISA plates coated with either LR55 or LR67 at 0.5 µg/ml respectively, and the absorbance values were plotted against the plasma dilutions. The antibody titer was defined as the plasma dilution, which gives an absorbance value of A492=1.00 in the parallel portion of the curves.

Results

Figure 7:
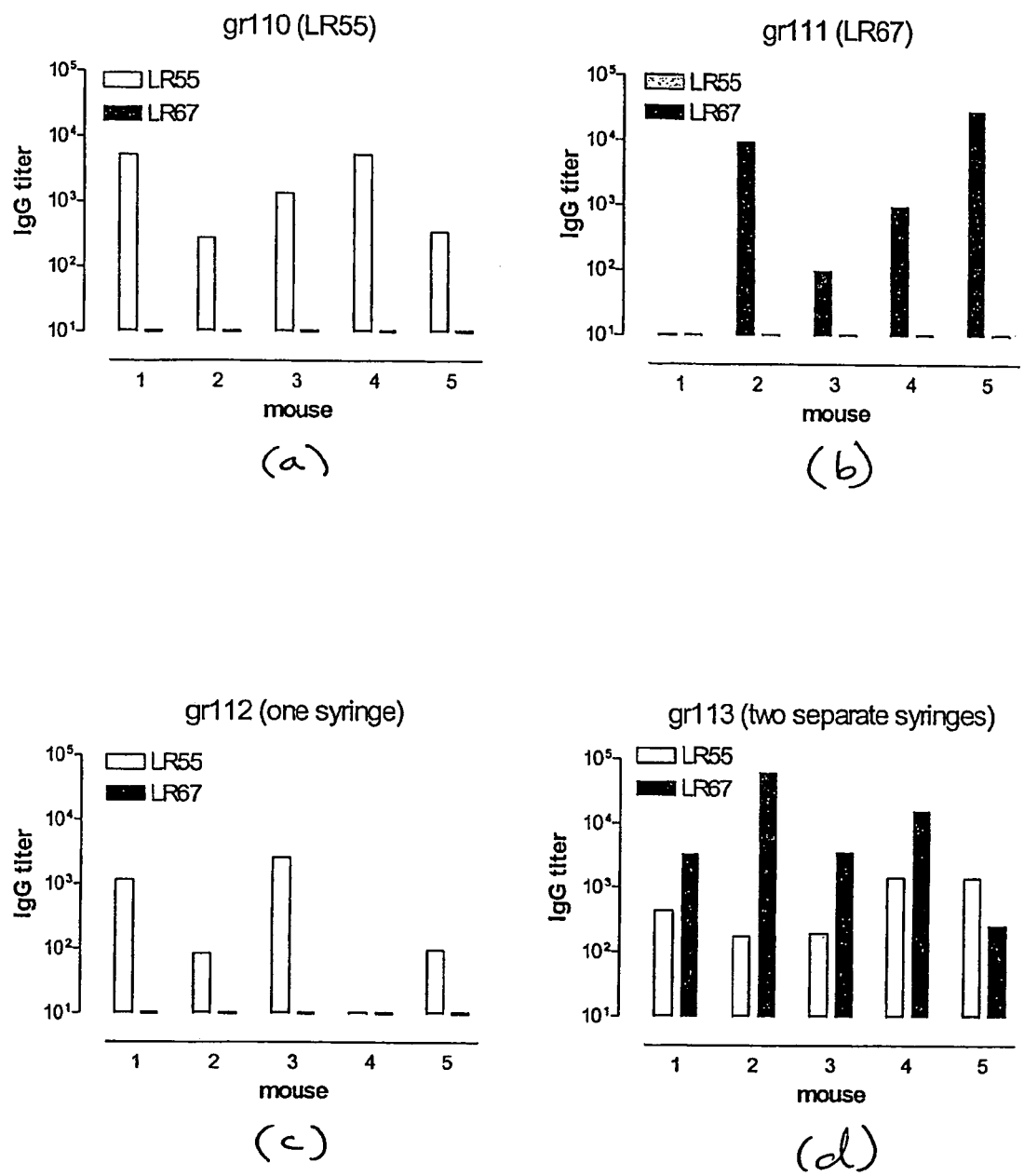

To determine whether it is feasible to obtain a balanced immune response against a mixture of MSP3 and GLURP produced as long synthetic peptides, four groups of BALBc mice were each immunized subcutaneously with 1) LR55 (gr110), 2) LR67 (gr111), 3) LR55 and LR67 combined in one syringe (gr 112) or 4) LR55 and LR67 injected separately at two different sites (gr113). Sera collected 35 days after the first injection, were tested for IgG antibody reactivity against GLURP and MSP3, respectively. Mice immunized with LR55 or LR67 alone reacted strongly with either LR55 of LR67, respectively (FIGS. 7(*a*) and 7(*b*)). Likewise, mice immunized with the two molecules injected at different sits reacted strongly with both GLURP and MSP3 domains (FIG. 7(*d*)) whereas mice immunized with a combination of the two molecules administered in one syringe reacted exclusively against LR55 (FIG. 7(*c*)).

This result strongly supports the notion that a mixture of individual GLURP and MSP3 products cannot be administered in a single vaccine formulation without antigen competition between GLURP and MSP3.

REFERENCES

1. Aribot, G., C. Rogier, J. L. Sarthou, J. F. Trape, A. T. Balde, P. Druilhe, and C. Roussilhon. 1996. Pattern of immunoglobulin isotype response to *Plasmodium falciparum* blood-stage antigens in individuals living in a holoendemic area of Senegal (Dielmo, west Africa). Am. J. Trop. Med. Hyg. 54:449457.
2. Aucan, C., Y. Traore, F. Tall, B. Nacro, T. Traore-Leroux, F. Fumoux, and P. Rihet. 2000. High immunoglobulin G2 (IgG2) and low IgG4 levels are associated with human resistance to *Plasmodium falciparum* malaria. Infect. Immun. 68:1252-1258.
3. Badell, E., C. Oeuvray, A. Moreno, Soe Soe, N. v. Rooijen, A. Bouzidi, and P. Druilhe. 2000. Human malaria in immunocompromised mice: an in vivo model to study defence mechanisms against *Plasmodium falciparum*. J. Exp. Med. 192:1653-1659.
4. Boudin, C., B. Chumpitazi, M. Dziegiel, F. Peyron, S. Picot, B. Hogh, and P. Ambroise-Thomas. 1993. Possible role of specific immunoglobulin M antibodies to *Plasmodium falciparum* antigens in immunoprotection of humans living in a hyperendemic area, Burkina Faso. J. Clin. Microbiol. 31:636-641.
5. Bouharoun-Tayoun, H., P. Attanath, A. Sabchareon, T. Chongsuphajaisiddhi, and P. Druilhe. 1990. Antibodies that protect humans against *Plasmodium falciparum* blood stages do not on their own inhibit parasite growth and invasion in vitro, but act in cooperation with monocytes. J. Exp. Med. 172:1633-1641.
6. Bouharoun-Tayoun, H., C. Oeuvray, F. Lunel, and P. Druilhe. 1995. Mechanisms underlying the monocyte-mediated antibody-dependent killing of *Plasmodium falciparum* asexual blood stages. J. Exp. Med. 182:409-418.
7. Bredmose, L., S. M. Madsen, A. Vrang, P. Ravn, M. G. Johnsen, J. Glenting, J. Arnau, and H. Israelsen. 2001. Development of a heterologous geneexpression system for use in *Lactococcus lactis*, p. 269-275. In O.-W. Merten (ed.), Recombinant Protein Production with Prokaryotic and Eukaryotic Cells. Kluwer Academic Publishers.
8. Carvalho, L. J. M. 2000. Instituto Oswaldo Cruz/Fiocruz. Evaluation of the immunogenicity and protective efficacy of *Plasmodium falciparum* MSP3 and GLURP in the neotropical primates *Saimiri sciureus* and *Aotus infulatus*.
9. Clark, J. T., S. Donachie, R Anand, C. F. Wilson, H. G. Heidrich, and J. S. McBride. 1989. 46-53 kilodalton glycoprotein from the surface of *Plasmodium falciparum* merozoites. Mol. Biochem. Parasitol. 32:15-24.
10. Cohen, S., A. McGregor, and S. Carrington. 1961. Gamma globulin and acquired immunity to human malaria. Nature 192:733-737.
11. Dodoo, D., M. Theisen, J. A. Kurtzhals, B. D. Akanmori, K A. Koram, S. Jepsen, F. K. Nkrumah, T. G. Theander, and L. Hviid. 2000. Naturally acquired antibodies to the glutamate-rich protein are associated with protection against *Plasmodium falciparum* malaria. J. Infect. Dis. 181:1202-1205.
12. Druilhe, P. and J. L. Perignon. 1994. Mechanisms of defense against *P. falciparum* asexual blood stages in humans. Immunol. Lett. 41:115-120.
13. Druilhe, P., A. Sabchareon, H. Bouharoun-Tayoun, C. Oeuvray, and J. L. Perignon. 1997. In vivo veritas: lessons from immunoglobulin-transfer experiments in malaria patients. Ann. Trop. Med. Parasitol. 91, Supp.:37-53.
14. Druilhe, P., A. Sabcharoen, H. Bouharoun-Tayoun, C. Oeuvray, and J. L. Perignon. 1997. In vivo veritas: lessons from immunoglobulin-transfer experiments in malaria patients. Ann. Trop. Med. Parasitol. 91, Supp.:37-53.
15. Dziegiel, M., P. Rowe, S. Bennett, S. J. Allen, O. Olerup, A. Gottschau, M. Borre, and E. M. Riley. 1993. Immunoglobulin M and G antibody responses to *Plasmodium falciparum* glutamate-rich protein: correlation with clinical immunity in Gambian children. Infect. Immun. 61:103-108.
16. Epping, R. J., S. D. Goldstone, L. T. Ingram, J. A. Upcroft, R. Ramasamy, J. A. Cooper, G. R. Bushell, and H. M. Geysen. 1988. An epitope recognised by inhibitory monoclonal antibodies that react with a 51 kilodalton merozoite surface antigen in *Plasmodium falciparum*. Mol. Biochem. Parasitol. 28:1-10.
17. Gasson, M. J. 1983. Plasmid complements of *Streptococcus lactis* NCDO 712 and other lactic *streptococci* after protoplast-induced curing. J. Bacteriol. 154:1-9.
18. Genton, B., F. Al Yaman, R. Anders, A. Saul, G. Brown, D. Pye, D. O. Irving, W. R. Briggs, A. Mai, M. Ginny, T. Adiguma, L. Rare, A. Giddy, R. Reber-Liske, D. Stuerchler, and M. P. Alpers. 2000. Safety and immunogenicity of a three-component blood-stage malaria vaccine in adults living in an endemic area of Papua New Guinea. Vaccine 18:2504-2511.
19. Gosselin, E. J., K. Wardwell, D. R. Gosselin, N. Alter, J. L. Fisher, and P. M. Guyre. 1992. Enhanced antigen presentation using human Fc gamma receptor (monocyte/macrophage)-specific immunogens. J. Immunol. 149:3477-3481.
20. Hisaeda, H., A. Saul, J. J. Reece, M. C. Kennedy, C. A. Long, L. H. Miller, and A. Stowers. 2002. Merozoite surface protein 3 and protection against malaria in *Aotus nancymai* monkeys. Journal of Infectious diseases 185:657-664.
21. Hogh, B., E. Petersen, M. Dziegiel, K. David, A. Hanson, M. Borre, A. Holm, J. Vuust, and S. Jepsen. 1992. Antibodies to a recombinant glutamate-rich *Plasmodium falciparum* protein: evidence for protection of individuals living in a holoendemic area of Liberia. Am. J. Trop. Med. Hyg. 46:307-313.
22. Holo, H. and L. F. Nes. 1995. Transformation of *Lactococcus* by electroporation. Methods Mol. Biol. 47:195-9.: 195-199.
23. Israelsen, H., S. M. Madsen, A. Vrang, E. B. Hansen, and E. Johansen. 1995. Cloning and partial characterization of regulated promoters from *Lactococcus lactis* Tn917-lacZ integrants with the new promoter probe vector, pAK80. Appl. Environ. Microbiol. 61:2540-2547.
24. Jensen, P. R. and K. Hammer. 1993. Minimal requirements for exponential growth in *Lactococcus lactis*. Appl. Environ. Microbiol. 59:4363-4366.
25. Keitel, W. A., K. E. Kester, R. L. Atmar, A. C. White, N. H. Bond, C. A. Holland, U. Krzych, D. R. Palmer, A. Egan, C. Diggs, W. R. Ballou, B. F. Hall, and D. Kaslow. 1999. Phase I trial of two recombinant vaccines containing the 19 kd carboxy terminal fragment of *Plasmodium falciparum* merozoite surface protein 1 (msp-1(19)) and T helper epitopes of tetanus toxoid. Vaccine 18:531-539.
26. Khusmith, S. and P. Druilhe. 1983. Antibody-dependent ingestion of *P. falciparum* merozoites by human blood monocytes. Parasite Immunol. 5:357-368.
27. Klausen, J., M. Magnusson, A. B. Andersen, and C. Koch. 1994. Characterization of purified protein derivative of tuberculin by use of monoclonal antibodies: isolation of a delayed-type hypersensitivity reactive component from *M. tuberculosis* culture filtrate. Scand. J. Immunol. 40:345-349.
28. Kussmann, M., U. Lassing, C. A. Sturmer, M. Przybylski, and P. Roepstorff. 1997. Matrix-assisted laser desorption/ionization mass spectrometric peptide mapping of the neural cell adhesion protein neurolin purified by sodium dodecyl sulfate polyacrylamide gel electrophoresis or acidic precipitation. J. Mass Spectrom. 32:483-493.
29. Lawrence, G., Q. Q. Cheng, C. Reed, D. Taylor, A. Stowers, N. Cloonan, C. Rzepczyk, A. Smillie, K. Anderson, D. Pombo, A. Allworth, D. Eisen, R. Anders, and A. Saul. 2000. Effect of vaccination with 3 recombinant asexual-stage malaria antigens on initial growth rates of *Plasmodium falciparum* in non-immune volunteers. Vaccine 18:1925-1931.
30. Locher, C. P. and L. Q. Tam. 1993. Reduction of disulfide bonds in *Plasmodium falciparum* gp195 abolishes the production of growth-inhibitory antibodies. Vaccine 11:1119-1123.
31. Lunel, F. and P. Druilhe. 1989. Effector cells involved in nonspecific and antibody-dependent mechanisms directed against *Plasmodium falciparum* blood stages in vitro. Infect. Immun. 57:2043-2049.
32. Madsen, S. M. 2000. The Technical University of Denmark. Characterization of regulated promoters from *Lactococcus*.
33. Madsen, S. M., J. Arnau, A. Vrang, M. Givskov, and H. Israelsen. 1999. Molecular characterization of the pH-inducible and growth phase-dependent promoter P170 of *Lactococcus lactis*. Mol. Microbiol. 32:75-87.
34. McColl, D. J. and R. F. Anders. 1997. Conservation of structural motifs and antigenic diversity in the *Plasmodium falciparum* merozoite surface protein-3 (MSP-3). Mol. Biochem. Parasitol. 90:21-31.
35. McColl, D. J., A. Silva, M. Foley, J. F. Kun, J. M. Favaloro, J. K. Thompson, V. M. Marshall, R. L. Coppel, D. J. Kemp, and R. F. Anders. 1994. Molecular variation in a novel polymorphic antigen associated with *Plasmodium falciparum* merozoites. Mol. Biochem. Parasitol. 68:53-67.
36. Oeuvray, C., H. Bouharoun-Tayoun, H. Gras-Masse, E. Bottius, T. Kaidoh, M. Aikawa, M. C. Filgueira, A. Tartar, and P. Druilhe. 1994. Merozoite surface protein-3: a malaria protein inducing antibodies that promote *Plasmodium falciparum* killing by cooperation with blood monocytes. Blood 84:1594-1602.
37. Oeuvray, C., Roussilhon, C., Perignon, J. L., Sarthou, J. L., Cisse, B., Tall, A., Diagne, N., and Druilhe, P. Natural immunity against *falciparum* malaria is strongly associated with IgG3 antibodies against the merozoite surface protein-3, in an age-independent manner. 2000. Cartagena, Colombia, XVth International Congress for Tropical Medicine and Malaria. Ref Type: Conference Proceeding
38. Oeuvray, C., M. Theisen, C. Rogier, J. F. Trape, S. Jepsen, and P. Druilhe. 2000. Cytophilic immunoglobulin responses to *Plasmodium falciparum* glutamate-rich protein are correlated with protection against clinical malaria in Dielmo, Senegal. Infect. Immun. 64:2617-2620.
39. Okenu, D. M. N., A. W. Thomas, and D. J. Conway. 2000. Allelic lineages of the merozoite surface protein 3 gene in *Plasmodium reichenowi* and *Plasmodium falciparum*. Mol. Biochem. Parasitol. 109:185-188.
40. Rolph, M. S. and L. A. Ramshaw. 1997. Recombinant viruses as vaccines and immunological tools. curr. Opin. Immunol. 9:517-524.

41. Sabchareon, A., T. Burnouf, D. Ouattara, P. Attanath, H. Bouharoun-Tayoun, P. Chantavanich, C. Foucault, T. Chongsuphajaisiddhi, and P. Druilhe. 1991. Parasitologic and clinical human response to immunoglobulin administration in *falciparum* malaria. Am. J. Trop. Med. Hyg. 45:297-308.

42. Sabchareon, A., T. Burnouf, D. Ouattara, P. Attanath, H. Bouharoun-Tayoun, P. Chantavanich, C. Foucault, T. Chongsuphajaisiddhi, and P. Druilhe. 1991. Parasitologic and clinical human response to immunoglobulin administration in *falciparum* malaria. Am. J. Trop. Med. Hyg. 45:297-308.

43. Saul, A., G. Lawrence, A. Smillie, C. M. Rzepczyk, C. Reed, D. Taylor, K. Anderson, A. Stowers, R. Kemp, A. Allworth, R. F. Anders, G. V. Brown, D. Pye, P. Schoofs, D. O. Irving, S. L. Dyer, G. C. Woodrow, W. R. Briggs, R. Reber, and D. Sturchler. 1999. Human phase I vaccine trials of 3 recombinant asexual stage malaria antigens with Montanide ISA720 adjuvant. Vaccine 17:3145-3159.

44. Shevchenko, A., M. Wilm, O. Vorm, and M. Mann. 1996. Mass spectrometric sequencing of proteins silver-stained polyacrylamide gels. Anal. Chem. 68:850-858.

45. Shi, Y. P., B. L. Nahlen, S. Kariuki, K. B. Urdahl, P. D. McElroy, J. M. Roberts, and A. A. Lal. 2001. Fc Receptor IIa (CD32)polymorphism is associated with protection of infants against high-density *Plasmodium falciparum* infection. VII. Asembo Bay Cohort Project. J. Infect. Dis. 184:107-111.

46. Simon, D. and A. Chopin. 1988. Construction of a vector plasmid family and its use for molecular cloning in *Streptococcus lactis*. Biochimie 70:559-566.

47. Soe Soe. 2000. Application of the antibody dependent cellular inhibition (ADCI) assay to the identification of protective antigens and the study of the establishment of protective immunity in Myanmar.

48. Stricker, K, J. Vuust, S. Jepsen, C. Oeuvray, and M. Theisen. 2000. Conservation and heterogeneity of the Glutamate-rich protein (GLURP) among field isolates and laboratory lines of *Plasmodium falciparum*. Mol. Biochem. Parasitol. 111:123-130.

49. Theisen, M., G. Cox, B. Hogh, S. Jepsen, and J. Vuust. 1994. Immunogenicity of the *Plasmodium falciparum* glutamate-rich protein expressed by vaccinia virus. Infect. Immun. 62:3270-3275.

50. Theisen, M., D. Dodoo, A. T. Balde, Soe Soe, Corradin G, K. A. Koram, J. Kurtzhals, T. G. Theander, B. D. Akanmori, G. Ndiaye, and P. Druilhe. 2001. Selection of long GLURP synthetic peptides for vaccine development: antigenicity, relationship with clinical protection and immunogenicity. Infect. Immun. 69:5223-5229.

51. Theisen, M., Soe Soe, S. Jessing, L. Okkels, S. Danielsen, C. Oeuvray, P. Druilhe, and S. Jepsen. 2000. Identification of a major linear B cell epitope of the *Plasmodium falciparum* Glutamate-rich protein (GLURP), targeted by human antibodies mediating parasite killing. Vaccine 19:204-212.

52. Theisen, M., Soe Soe, C. Oeuvray, A. W. Thomas, J. Vuust, S. Danielsen, S. Jepsen, and P. Druilhe. 1998. The glutamate-rich protein (GLURP) of *Plasmodium falciparum* is a target for antibody-dependent monocyte-mediated inhibition of parasite growth in vitro. Infect. Immun. 66:11-17.

53. Theisen, M., A. W. Thomas, and S. Jepsen. 2001. Nucleotide sequence and analysis of the gene encoding the glutamate-rich protein (GLURP) from *Plasmodium, reichenowi*. Mol. Biochem. Parasitol. 115:269-273.

54. Theisen, M., J. Vuust, A. Gottschau, S. Jepsen, and B. Hogh. 1995. Antigenicity and immunogenicity of recombinant glutamate-rich protein of *Plasmodium falciparum* expressed in *Escherichia coli*. Clin. Diagn. Lab. Immunol. 2:30-34.

55. Thomas, A. W., J. A. Deans, G. H. Mitchell, T. Alderson, and S. Cohen. 1984. The Fab fragments of monoclonal IgG to a merozoite surface antigen inhibit *Plasmodium knowlesi* invasion of erythrocytes. Mol. Biochem. Parasitol. 13:187-199.

56. Warmerdam, P. A., J. G. van de Winkel, A. Vlug, N. A. Westerdaal, and P. J. Capel. 1991. A single amino acid in the second Ig-like domain of the human Fc gamma receptor II is critical for human IgG2 binding. J. Immunol. 147: 1338-1343.

57. WHO. 1999. Malaria, 1982-97. Weekly Epidemiol Record 74:265-272.

The invention claimed is:

1. A fusion protein comprising SEQ ID NO:1.

2. The fusion protein according to claim 1 further comprising a *Plasmodium falciparum* protein genetically coupled thereto, wherein said *Plasmodium falciparum* protein is selected from the group consisting of circumsporozoite protein (CS), merozoite surface protein 1 (MSP1), merozoite surface protein 2 (MSP2), merozoite surface protein 3 (MSP3), merozoite surface protein 4 (MSP4), merozoite surface protein 5 (MSP5), merozoite surface protein 6 (MSP6), apical membrane antigen (AMA1), Pf155/ring-infected erythrocyte surface antigen (Pf155/RESA), Rhoptry-associated protein (RAP1), Erythrocyte-binding antigen 175 (EBA-175), *Plasmodium falciparum* erythrocyte membrane protein (pfEMP1), exported protein 1 (EXP1), Liver-stage antigen 1 (LSA1), Liver-stage and antigen 3 (LSA3), Pf25, Pf45/48, Pf230, Pf27, Pf16 and Pf28.

3. An immunogenic composition comprising a fusion protein that comprises a *Plasmodium falciparum* Glutamate-rich protein (GLURP) joined to a *Plasmodium falciparum* protein selected from the group consisting of circumsporozoite protein (CS), merozoite surface protein 1 (MSP1), merozoite surface protein 2 (MSP2), merozoite surface protein 3 (MSP3), merozoite surface protein 4 (MSP4), merozoite surface protein 5 (MSP5), merozoite surface protein 6 (MSP6), apical membrane antigen (AMA1), Pf155/ring-infected erythrocyte surface antigen (Pf155/RESA), Rhoptry-associated protein (RAP1), Erythrocyte-binding antigen 175 (EBA-175), *Plasmodium falciparum* erythrocyte membrane protein (pfEMP1), exported protein 1 (EXP1), Liver-stage antigen 1 (LSA1), Liver-stage and antigen 3 (LSA3), Pf25, Pf45/48, Pf230, Pf27, Pf16 and Pf28 protein, wherein said fusion protein comprises the sequence of SEQ ID NO. 1.

4. A fusion protein consisting essentially of the sequence of SEQ. ID. NO. 1.

5. A fusion protein consisting of the sequence of SEQ. ID. NO. 1.

* * * * *